United States Patent
Kokai et al.

(10) Patent No.: US 9,750,851 B2
(45) Date of Patent: Sep. 5, 2017

(54) IMPLANTABLE MEDICAL DEVICES HAVING DOUBLE WALLED MICROSPHERES

(71) Applicant: University Of Pittsburgh—Of The Commonwealth System Of Higher Education, Pittsburgh, PA (US)

(72) Inventors: Lauren Elizabeth Kokai, Santa Barbara, CA (US); Kacey Gribbin Marra, Canonsburg, PA (US)

(73) Assignee: University of Pittsburgh—of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 15/334,625

(22) Filed: Oct. 26, 2016

(65) Prior Publication Data

US 2017/0043059 A1   Feb. 16, 2017

Related U.S. Application Data

(60) Division of application No. 13/788,879, filed on Mar. 7, 2013, now Pat. No. 9,498,221, which is a continuation of application No. PCT/US2011/051053, filed on Sep. 9, 2011.

(60) Provisional application No. 61/381,725, filed on Sep. 10, 2010.

(51) Int. Cl.
| | |
|---|---|
| *A61L 27/58* | (2006.01) |
| *A61K 9/50* | (2006.01) |
| *A61L 27/18* | (2006.01) |
| *A61L 27/54* | (2006.01) |
| *B01J 13/22* | (2006.01) |
| *A61K 38/18* | (2006.01) |
| *A61B 17/11* | (2006.01) |
| *A61M 37/00* | (2006.01) |
| *A61K 9/00* | (2006.01) |

(52) U.S. Cl.
CPC .......... *A61L 27/58* (2013.01); *A61B 17/1128* (2013.01); *A61K 9/50* (2013.01); *A61K 38/185* (2013.01); *A61L 27/18* (2013.01); *A61L 27/54* (2013.01); *A61M 37/00* (2013.01); *B01J 13/22* (2013.01); *A61K 9/0024* (2013.01); *A61K 9/5031* (2013.01); *A61L 2300/414* (2013.01); *A61L 2430/32* (2013.01); *A61M 2205/04* (2013.01)

(58) Field of Classification Search
CPC ...... A61K 9/0024; A61K 9/50; A61K 9/5031; A61K 38/185; A61L 27/18; A61L 27/54; A61L 2430/32; A61L 27/58; A61L 2300/414; A61M 37/00; A61M 2205/04; B01J 13/22; C08L 67/04; A61B 17/1128
See application file for complete search history.

(56) References Cited

U.S. PATENT DOCUMENTS

| | | | |
|---|---|---|---|
| 5,985,354 A | 11/1999 | Mathiowitz et al. | |
| 9,498,221 B2 | 11/2016 | Kokai et al. | |
| 2001/0031974 A1* | 10/2001 | Hadlock ............ | A61B 17/1128 606/152 |
| 2006/0051425 A1 | 3/2006 | Kvitnitsky et al. | |
| 2006/0233782 A1 | 10/2006 | Gruskin et al. | |
| 2011/0027376 A1* | 2/2011 | Boey ................. | A61K 9/107 424/499 |

FOREIGN PATENT DOCUMENTS

| | | |
|---|---|---|
| WO | WO 2009/075652 A1 | 6/2009 |
| WO | WO 2010/010223 A1 | 1/2010 |

OTHER PUBLICATIONS

U.S. Appl. No. 13/788,879, Oct. 17, 2016 Issue Fee Payment.
U.S. Appl. No. 13/788,879, Jul. 20, 2016 Notice of Allowance.
U.S. Appl. No. 13/788,879, Jun. 23, 2016 Response to Non-Final Office Action.
U.S. Appl. No. 13/788,879, Feb. 23, 2016 Non-Final Office Action.
U.S. Appl. No. 13/788,879, Jan. 6, 2016 Amendment and Request for Continued Examination (RCE).
U.S. Appl. No. 13/788,879, Nov. 9, 2015 Response after Final Action.
U.S. Appl. No. 13/788,879, Jul. 8, 2015 Final Office Action.
U.S. Appl. No. 13/788,879, Apr. 8, 2015 Response to Non-Final Office Action.
U.S. Appl. No. 13/788,879, Jan. 9, 2015 Non-Final Office Action.
U.S. Appl. No. 13/788,879, Dec. 15, 2014 Response to Restriction Requirement.
U.S. Appl. No. 13/788,879, Sep. 15, 2014 Restriction Requirement.
Barras, et al., "Glial Cell Line-Derived Neurotrophic Factor Released by Synthetic Guidance Channels Promotes Facial Nerve Regeneration in the Rat", J. Neurosci. Res., 70(6):746-755 (2002).
Brown, et al., "Self-Evaluation of Walking-Track Measurement Using a Sciatic Function Index", Microsurgery, 10(3):226-235 (1989).
Di Scipio, et al., "A Simple Protocol for Paraffin-Embedded Myelin Sheath Staining with Osmium Tetroxide for Light Microscope Observation", Microsc. Res. Tech., 71(7):497-502 (2008).
Fine, et al., "GDNF and NGF released by Synthetic Guidance Channels support Sciatic Nerve Regeneration Across a Long Gap", Eur. J. Nueroscri., 15(4):589-601 (2002).
Guénard, et al., "Syngeneic Schwann Cells Derived from Adult Nerves Seeded in Semipermeable Guidance channels Enhance Peripheral Nerve Regeneration", J. Neurosci., 12(9):3310-3320 (1992).
Hunter, et al., "Binary Imaging Analysis for Comprehensive Quantitative Histomorphometry of Peripheral Nerve", J. Neurosci. Methods, 166(1):116-124 (2007).
Iannotti, et al., "Glial Cell Line-Derived Neurotrophic Factor-Enriched Bridging Transplants Promote Propriospinal Axonal Regeneration and Enhanced Myelination After Spinal Cord Injury", Exp. Neurol., 183(2):379-393 (2003).

(Continued)

*Primary Examiner* — Suzanne Ziska
(74) *Attorney, Agent, or Firm* — Baker Botts LLP

(57) ABSTRACT

An implantable medical device including at least one double-walled microsphere containing an active agent, and a biodegradable polymer layer containing the at least one double-walled microsphere.

3 Claims, 20 Drawing Sheets

(56) References Cited

OTHER PUBLICATIONS

International Search Report for PCT/US11/051053, dated Apr. 25, 2012.
Iwase, et al., "Glial Cell Line-Derived Neurotrophic Factor-Induced Signaling in Schwann Cells", J. Neurochem., 94(6):1488-1499 (2005).
Jiang, et al., "Intravitreal Injections of GDNF-Loaded Biodegradable Microspheres are Neuroprotective in a Rat Model of Glaucoma", Molecular Vision, 13:1783-1792 (2007).
Kim, et al., "Peripheral Nerve Regeneration Using a Three Dimensionally Cultured Schwann Cell Conduit", J. Craniofac. Sur., 18(3):475-488 (2007).
Kokai et al., 2011, Sustained Growth Factor Delivery Promotes Axonal Regeneration in Long Gap Peripheral Nerve Repair, Tissue Engineering Part A, 17: 1263.
Kokai et al., Mar. 17, 2009, Diffusion of Soluble Factors Through Degradable Polymer Nerve Guides: Controlling Manufacturing Parameters, Acta Biomat. 5: 2540-2550.
Kokai et al., Sep. 11, 2009, Protein Bioactivity and Polymer Orientation is affected by Stabilizer Incorporation for Double-Walled Microspheres; J. Controlled. Rel. 141:168-176.
Kokai, 2009, Controlled Delivery Systems for Neuronal Tissue Engineering; Thesis, University of Pittsburgh.
Kokai, et al., "Incorporation of Double-Walled Microspheres into Polymer Nerve Guides for the Sustained Delivery of Glial Cell Line-Derived Neurotrophic Factor", Biomaterials, 31(8):2313-2322 (2010).
Kokai, et al., "Sustained Delivery of GDNF for Improved Peripheral Nerve Regeneration in a Sciatic Nerve Injury", Society for Biomaterials Annual Meeting, Seattle, Washington, Apr. 22, 2010, 1 pg.
Li, et al., "Nerve Conduit Filled with GDNF Gene-Modified Schwann Cells Enhances Regeneration of the Peripheral Nerve", Microsurgery, 26(2):116-121 (2006).
Li, et al., "Rescue of Adult Mouse Motoneurons from Injury-Induced Cell Death by Glial Cell Line-Derived Neurotrophic Factor", PNAS, 92(1):9771-9775 (1995).
Patel, et al., "GDNF-Chitosan Blended Nerve Guides: A Functional Study", Journal of Tissue Engineering and Regenerative Medicine, 1(5):360-367 (2007).
Pfister, et al., "Nerve conduits and Growth factor Delivery in Peripheral Nerve Repair", J. Peripher Nerv Syst., 12(2):65-82 (2007).
Rutkowski, et al., "Synergistic Effects of Micropatterned Biodegradable Conduits and Schwann Cells on Sciatic Nerve Regeneration", J. Neural Eng., 1(3):151-157 (2004).
Schlosshauer, et al., "Synthetic Nerve Guide Implants in Humans: A Comprehensive Survey", Neurosurgery, 59(4):740-474 (2006).
Valero-Cabré, et al., "Superior Muscle Reinnervation After Autologous Nerve Graft or Poly-L-Lactide-Episilon-Caprolactone (PLC) Tube Implantation in Comparison to Silicone Tube Repair", J. Neuroscience Res., 63(2):214-223 (2001).

\* cited by examiner

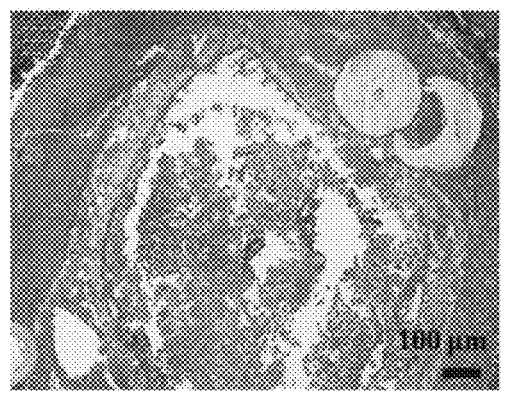
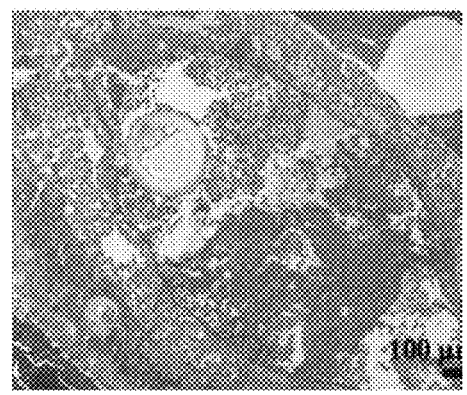
FIG. 17A      FIG. 17B
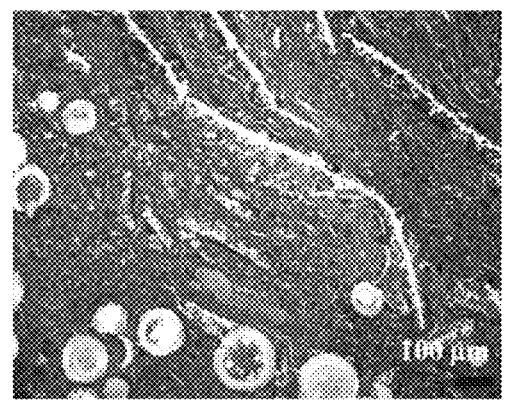
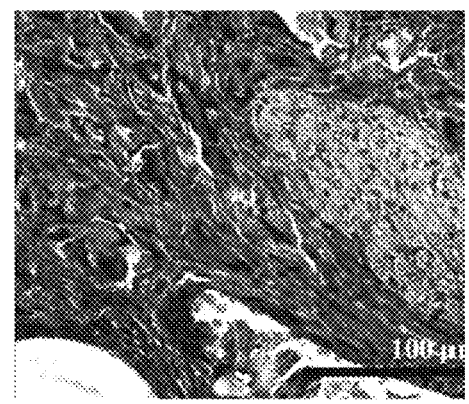
FIG. 17C      FIG. 17D
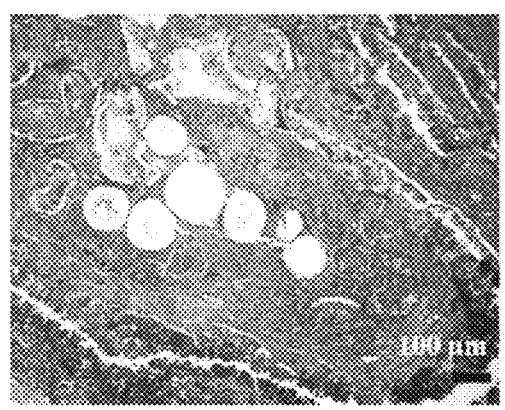
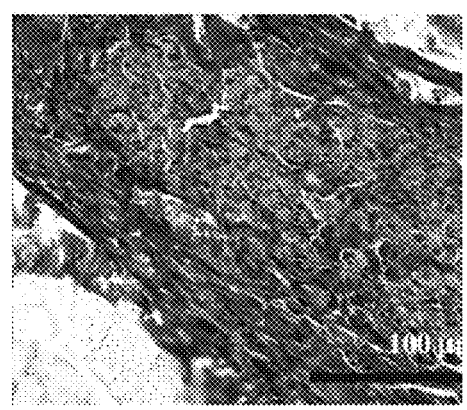
FIG. 17E      FIG. 17F

IMPLANTABLE MEDICAL DEVICES HAVING DOUBLE WALLED MICROSPHERES

PRIORITY CLAIM

This application is a divisional application of U.S. patent application Ser. No. 13/788,879 filed Mar. 7, 2013, which is a continuation of International Application Serial No. PCT/US2011/051053 filed Sep. 9, 2011, which claims priority to U.S. Provisional Application Ser. No. 61/381,725 filed Sep. 10, 2010, to each of which priority is claimed and the contents of each of which are incorporated by reference herein in their entireties.

GRANT INFORMATION

This invention was made with government support under grants DMR-0705948 awarded by the National Science Foundation and W81XWH-07-1-0716, awarded by the Department of Defense. The government has certain rights in the invention.

1. INTRODUCTION

The present invention relates to implantable medical devices (e.g., nerve guides) having double walled microspheres.

2. BACKGROUND

Though there has been a considerable amount of research in improving peripheral nerve guide design, commercially available nerve guides have not equaled the regenerative capacity of the nerve autograft in long gap peripheral nerve repair. While autografts (e.g., the sural nerve) have been used to bridge nerve defects of 6 cm or more (Kim et al., 2008, "Nerve Injuries: operative results from major nerve injuries, entrapments, and tumors. 2nd ed. Philadelphia: Saunders Elsevier. pp. 1-611), polymer based nerve guides are effectively used to regenerate nerves in gaps that span only 3 cm or less (Schlosshauer et al., 2006, Neurosurgery 59(4):740-748). This barrier in gap length may reflect the unmet need for nerve guides to actively promote nerve regeneration through the lumen of the guide from the proximal to the distal nerve stump (Kemp et al., 2008, Neurol. Res. 30:1030-1038).

In addition to providing mechanical support for regenerating nerves, nerve guides should also provide cues that guide axonal growth and increase the rate at which nerves regenerate.

The complex problem of targeting axonal outgrowth has led to the investigation of a variety of nerve guide materials, luminal fillers, cell therapies and combinations thereof (Midha et al., 2003, J. Neurosurg. 99(3):555-565). One additional pathway toward enhancing axonal growth involves locally delivering drugs or neurotrophic factors that promote nerve growth and survival. Growth factors have been delivered from nerve guides by adsorbing the growth factor to the nerve guide scaffold, incorporating growth factors into the scaffold material during fabrication (Chavez-Delgada et al., 2003, J. Biomed. Mater. Res. B. Appl. Biomater. 67B(2):702-711; Yang et al., 2005, J. Control Release 104(3):433-446), embedding growth factor loaded rods or microspheres into the nerve guide (Fine et al., 2002, Eur. J. Neurosci. 15(4):589-601; Bloch et al., 2001, Exp. Neurol. 172(2):425-432; Xu et al., 2003, Biomater. 24(13):2405-2412; Rosner et al., 2003, Ann. Biomed. Eng. 31(11):1383-1401; Goraltchouk et al., 2006, J. Control Release 110(2):400-407; Singh et al., 2008, Tissue Eng Part C Methods 14(4):299-309; Dodla et al., 2008, Biomaterials 29(1):33-46), covalently immobilizing growth factors onto the nerve guide surface (Chen et al., 2006, J. Biomed. Mater. Res. A. 79A(4):846-857; Wood et al., 2009, J. Biomed. Mater Res A 89A(4):909-918; Lee et al., 2003, Exp. Neurol. 184(1):295-303), or by implantation of an osmotic pump (Newman et al., 1996, Arch Otolaryngol Head Neck Surg 122(4):399-403; Lewin et al., 1997, Laryngoscope 107(7): 992-999) (for review of these techniques, see Kemp et al., 2008, Neurol. Res. 30:1030-1038 and Willerth et al., 2007, Adv. Drug Deliv. Rev. 59(4-5):325-338). Results from these preclinical studies have shown beneficial effects of delivered growth factors for nerve regeneration. For example, the delivery of nerve growth factor (NGF) promotes sensory neuron survival, outgrowth and branching (Bloch et al., 2001, Exp. Neurol. 172(2):425-432), ciliary neurotrophic factor (CNTF) aids in motor neuron survival and outgrowth (Xu et al., 2009, J. Clin. Neurosci. 16(6):812-817) and glial cell line-derived neurotrophic (GDNF) has been shown to promote the regeneration of fibers originating from the spinal cord beyond what has been measured with NGF (Fine et al., 2002, Eur. J. Neurosci. 15(4):589-601). Because of the promising reports following treatment of nerve injuries with neurotrophic factors, the delivery of such factors can be a potential method of surpassing the current length limitations in nerve regeneration. While strategies have been developed for protein delivery from polymer nerve guides, many conduit delivery systems lack a sustained and controlled release rate of bioactive proteins for the entire duration required for the axon to cross from the proximal to the distal nerve stump. Accordingly, there remains a need for nerve guides and other medical devices that can deliver an active agent for therapeutically effective periods.

3. SUMMARY

One embodiment of the presently disclosed subject matter provides an implantable medical device that includes double-walled microspheres containing an active agent, and a biodegradable polymer containing the double-walled microsphere. In one embodiment, the double-walled microsphere can include a poly(lactide) wall and a poly(lactic-co-glycolic acid) wall, where the active agent is a neurotrophic factor, such as glial cell-line derived neurotrophic factor (GDNF) or glial growth factor 2 (GGF2). The biodegradable polymer layer can include poly(caprolactone), and double walled microspheres can be embedded in the biodegradable polymer layer. A second biodegradable polymer can further be applied to the biodegradable polymer layer containing the at least one double-walled microsphere, and, without limitation can encapsulate the first, microsphere-containing polymer. In one embodiment, the medical device is a nerve guide.

Another embodiment of the presently disclosed subject matter provides a method of making an implantable medical device that includes forming a first mixture (e.g., a solution) of a first polymer and a first solvent, forming a second mixture (e.g., a solution) of a second polymer and a second solvent, adding an active agent to the first mixture and/or the second mixture, combining the first mixture and the second mixture to form a third mixture, introducing the third mixture to a third solvent to form microspheres, isolating the microspheres from the third solvent, and introducing the isolated microspheres into a biodegradable polymer layer. In one embodiment, the first mixture and the second mixture are combined by vortexing to form the third mixture, and the third mixture is added dropwise to the third solvent. In one embodiment, an emulsion is formed upon combining the first and second mixture. The microspheres can be isolated from the third solvent by centrifugation.

In one embodiment, the first polymer is poly(lactic-co-glycolic acid) and/or the second polymer is poly(lactide) (e.g. poly(L-Lactide)). The active agent is a neurotrophic factor, such as GDNF or GGF2.

Another embodiment of the present application provides an implantable nerve guide that includes double-walled microspheres with a neurotrophic factor active agent encapsulated therein, the double walled comprised of a poly (lactide) layer ("wall") and a poly(lactic-co-glycolic acid) layer ("wall"), a poly(caprolactone) polymer layer containing the double-walled microspheres; and a second poly (caprolactone) layer that at least partially encapsulates the biodegradable polymer layer containing the double-walled microspheres. In one embodiment, the nerve guide releases GDNF or GGF2 for at least 50 days following implantation in a human.

Another embodiment of the present application provides a method of promoting nerve generation comprising implanting an implantable medical device or an implantable nerve guide, as those medical devices and nerve guides are described herein. Yet another embodiment provides an implantable medical device or an implantable nerve guide prepared by any one of the processes described herein.

4. BRIEF DESCRIPTION OF THE FIGURES

Figure 2A:
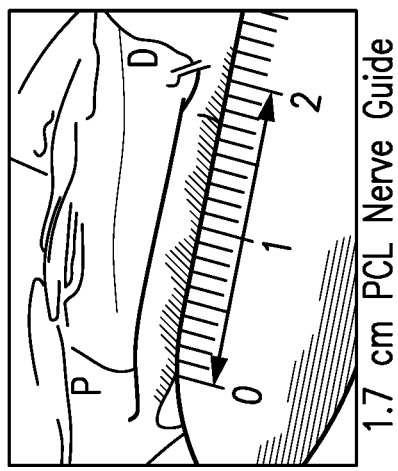

FIG. 2a is a photograph of PCL guide at time of implantation. Ruler indicates nerve guide is 1.7 cm in length. Nerve stumps were inserted 1 mm into each end of nerve guide.

Figure 2B:
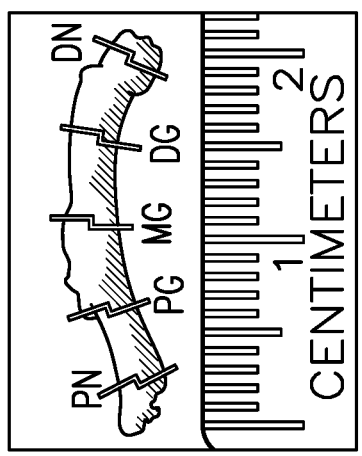

FIG. 2b is a photograph of explanted nerve and conduit at 6 weeks. Guide has been fixed and treated with osmium tetroxide. Dashed likes indicate position on guide where transverse cuts were made for histology.

Figure 2C:
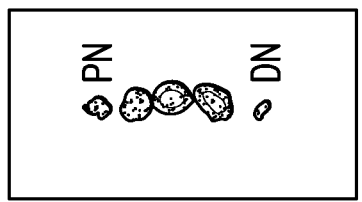

FIG. 2c is a photograph of sectioned nerve guide embedded in paraffin.

Figure 3A:
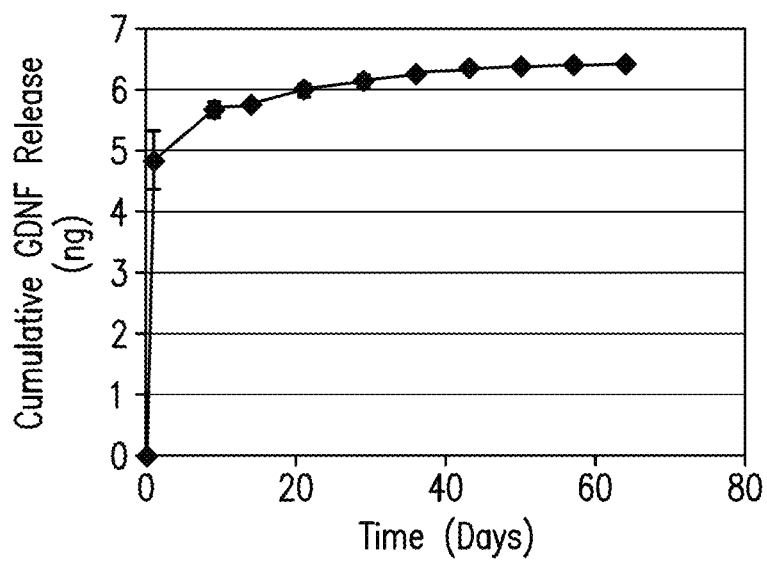

FIG. 3a depicts the cumulative release of GDNF from double-walled microspheres (mean±stdev, n=4 for 1 batch).

Figure 3B:
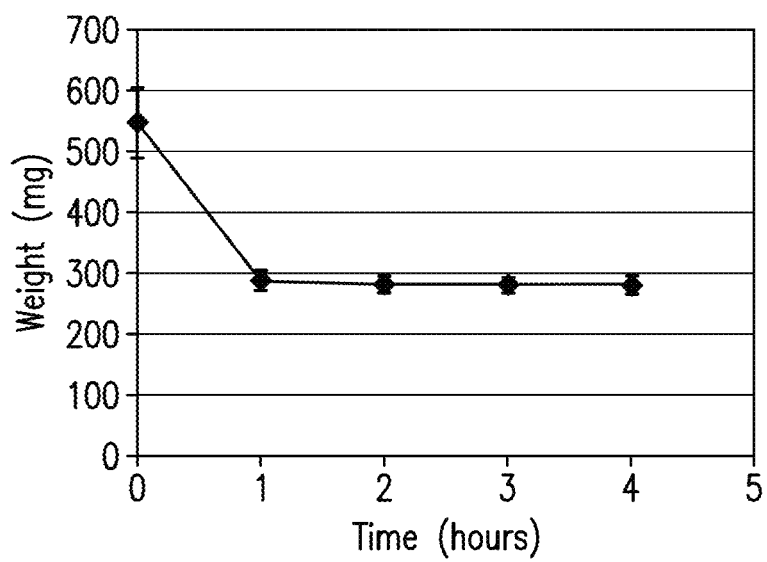

FIG. 3b depicts the weight of nerve guides following NaCl impregnation and removal by leaching in distilled water for specified time points. (Mean±stdev, N=5).

Figure 3C:
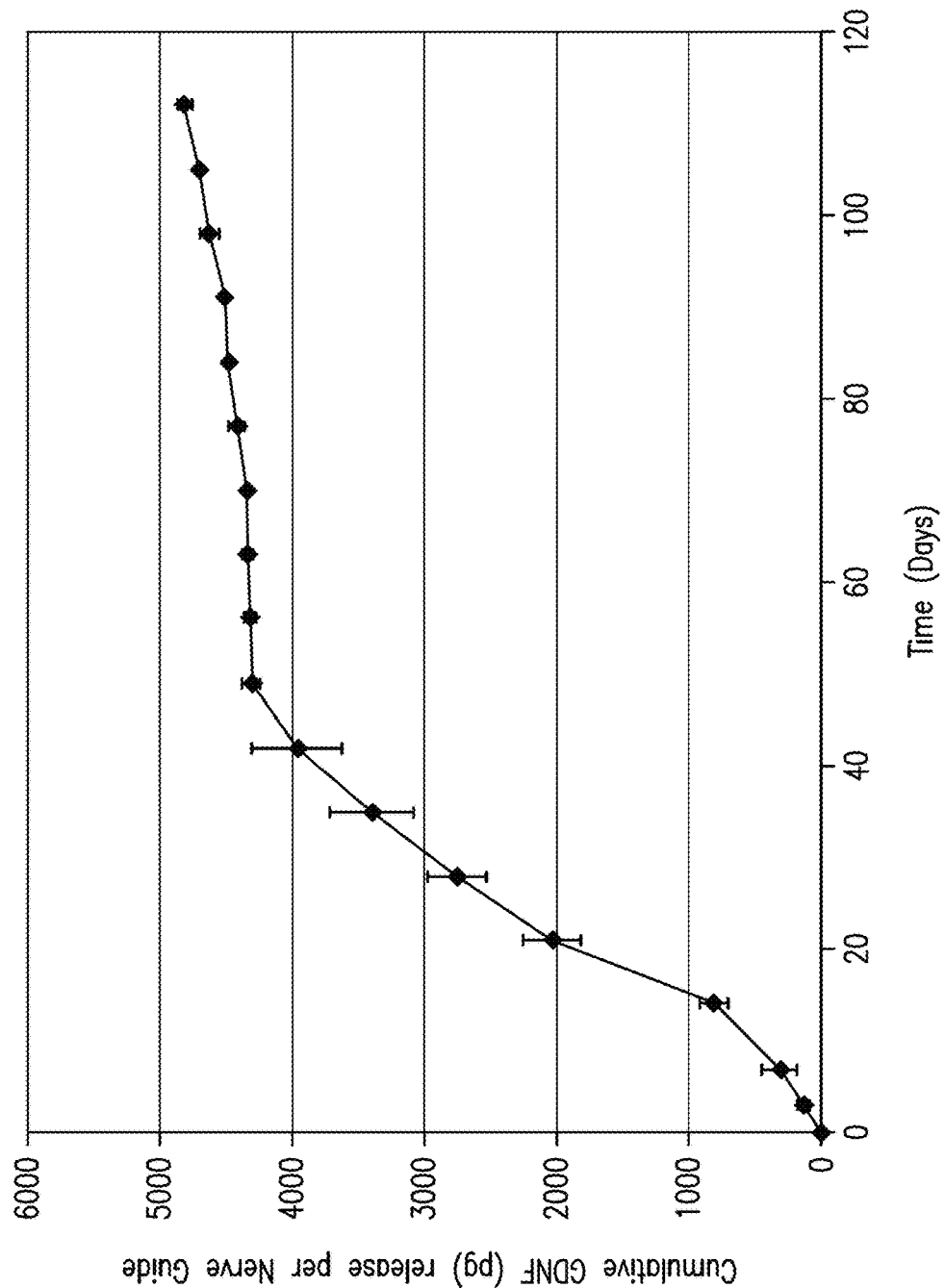

FIG. 3c depicts the cumulative release of the GDNF (pg) per individual nerve guide (1.7 cm in length), with values expressed as mean±std. dev. (n=4).

Figure 4A:
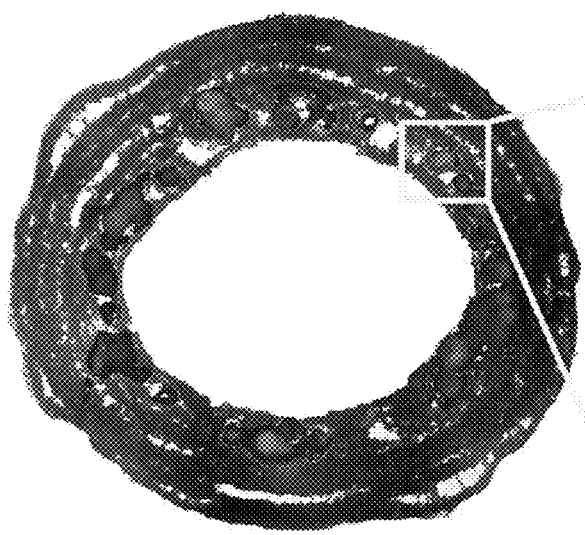

FIG. 4a is a compilation of brightfield and fluorescent micrographs taken at 10×. Multiple images of both the nerve guide and FITC-BSA encapsulated in double-walled microspheres were used to overlay fluorescent images on brightfield prior to realignment of figures.

Figure 4B:
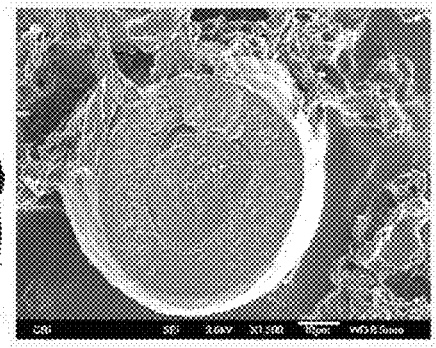

FIG. 4b is a scanning electron micrograph of double-walled microsphere following incorporation into PCL nerve guides.

Figure 5A:
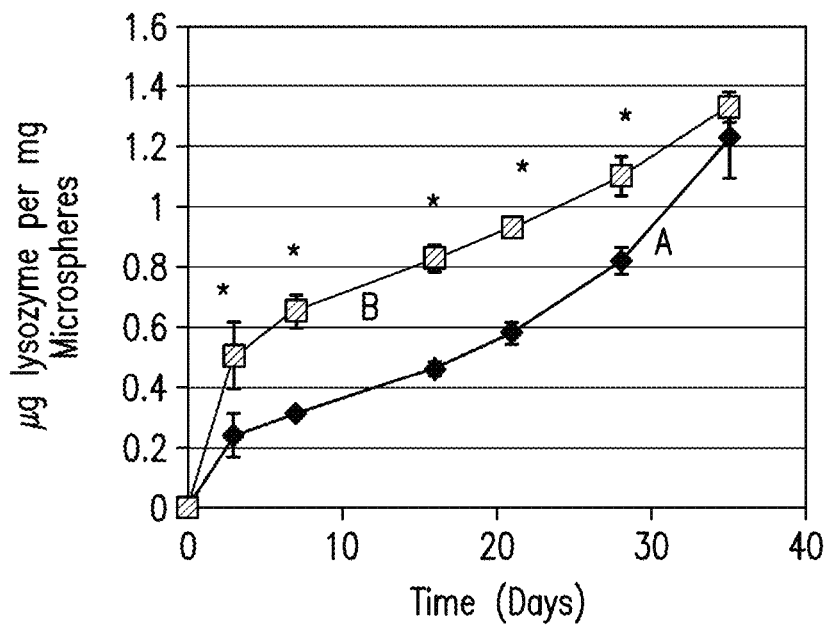

FIG. 5a depicts the cumulative release of lysozyme from PCL disks (A, diamonds) and microspheres suspended in buffer solution (B, squares) (mean±stdev, N=5). Asterisks indicate statistical differences between microspheres that were suspended in solution and those embedded in disks ($p<0.05$).

Figure 5B:
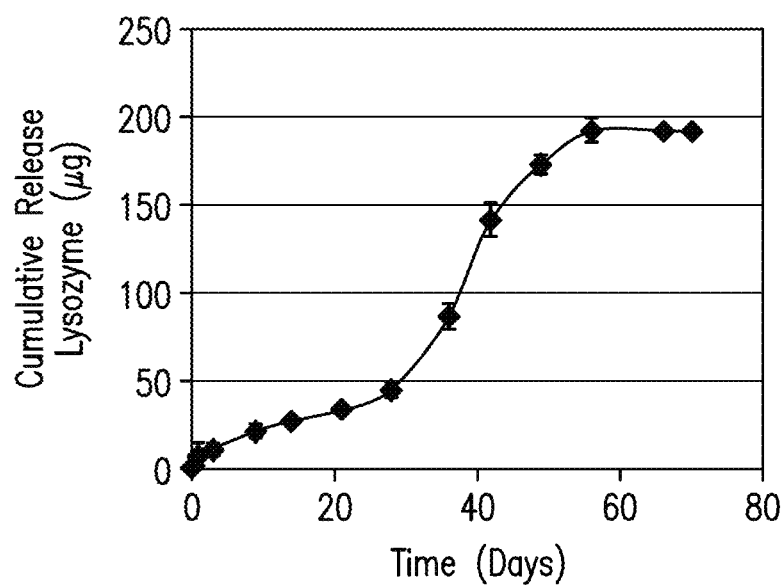

FIG. 5b depicts the cumulative release of lysozyme from nerved guides with double-walled microspheres (mean±stdev, n=5).

Figure 6A:
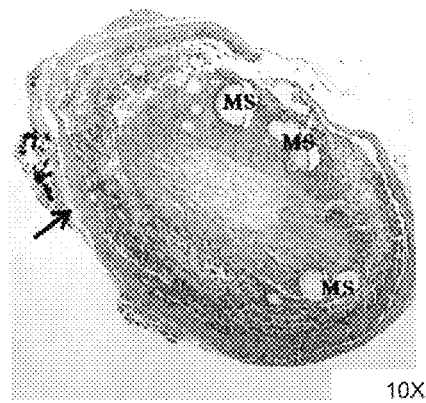
Figure 6B:

FIGS. 6a and 6b are a compilation of brightfield micrographs taken of a transverse section of the proximal segment guides visualized with Masson's trichrome stain. To create the final image, a series of 10× images were realigned and blended using photoshop CS3. FIG. 6A depicts negative control guides. Microspheres are labeled as "MS." The collagen capsule surrounding the implanted guide is labeled with an arrow. FIG. 6B depicts guides releasing GDNF.

Figure 6C:
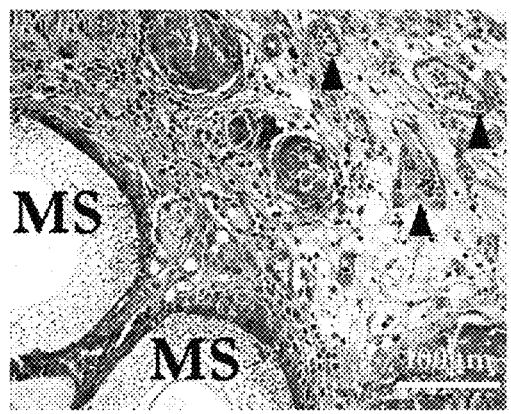
Figure 6D:
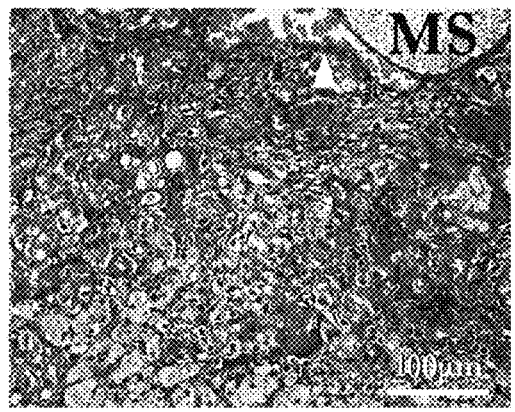

FIGS. 6c and 6d are high magnification brightfield micrographs taken of the lumen of explanted nerve guides from negative controls (FIG. 6c) and guides releasing GDNF (FIG. 6d). Blood vessels are labeled with an arrow head. Scale bars are 100×.

Figure 7A:
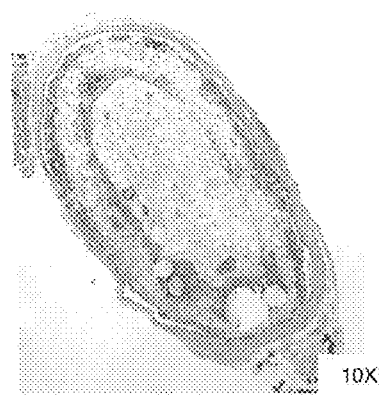
Figure 7B:
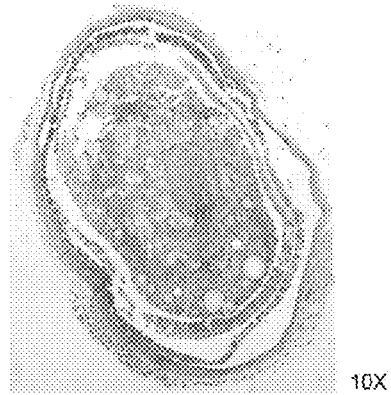

FIGS. 7a and 7b are compilation of brightfield micrographs taken of a transverse section of the distal segment of guides visualized with Masson's trichrome stain. FIG. 7A depicts the negative control guides and FIG. 7b depicts guides with GDNF.

Figure 7C:
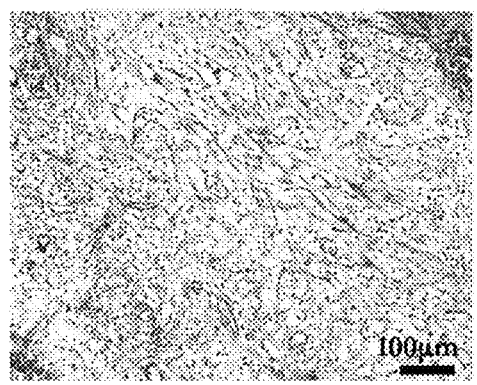
Figure 7D:
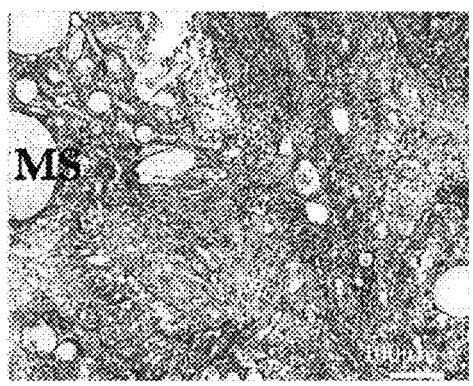

FIGS. 7c and 7d depict high magnification brightfield micrographs taken of the lumen of explanted nerve guides from negative controls (FIG. 7c) and guides releasing GDNF (FIG. 7d). Scale bars are 100 µm.

Figure 8A:
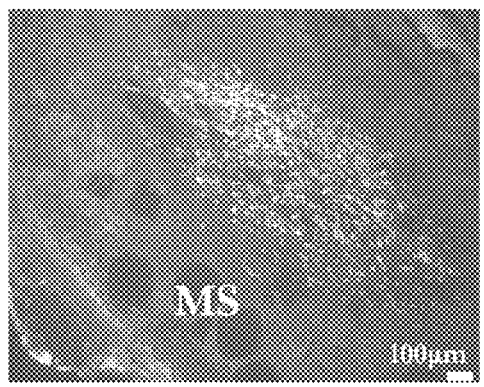
Figure 8B:
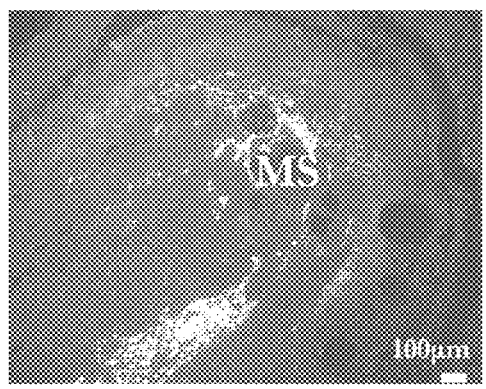

FIGS. 8a and 8b are black and white fluorescent micrograph showing Schwann cells (visualized with S100). Scale bars are 100 µm. FIG. 8a depicts the proximal transverse section of negative control guides. FIG. 8b depicts the proximal section of guides release GDNF.

Figure 8C:
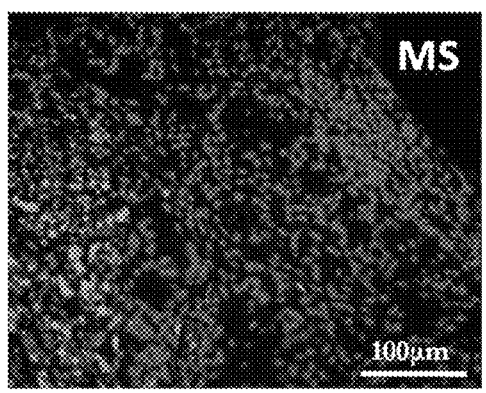
Figure 8D:
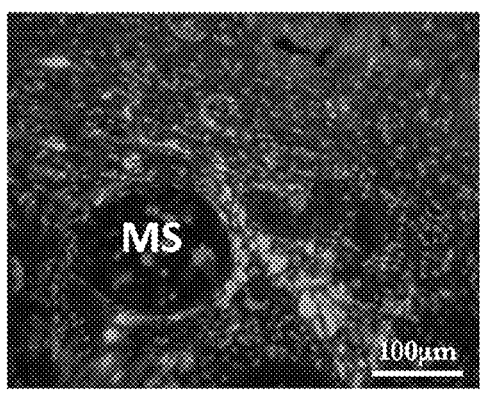

FIG. 8c depicts high magnification fluorescent micrograph of negative control nerve guide. FIG. 8d depicts high magnification fluorescent micrograph of double-walled microsphere encapsulating GDNF. Red indicates S100 labeling of Schwann cells. Dapi is blue.

Figure 9A:
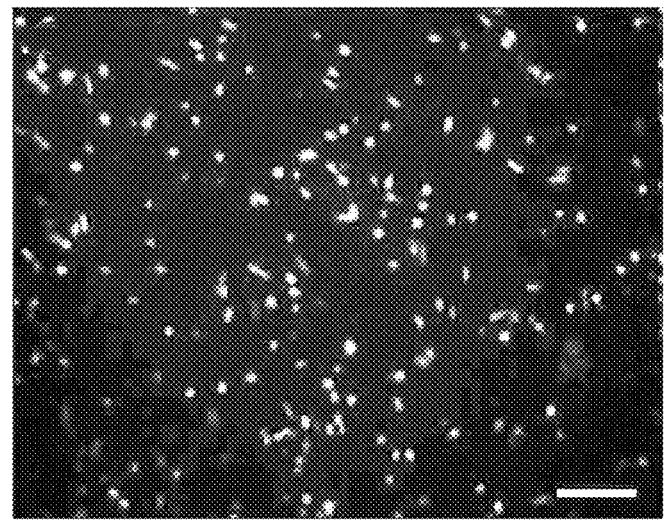
Figure 9B:

FIGS. 9a and 9b are fluorescent micrographs from distal segment of explanted nerve tissue for a negative control (FIG. 9a) and a guide implanted with encapsulated GDNF (FIG. 9b). Red indicates S100 protein in Schwann cells and Blue is DAPI nuclei stain.

Figure 10C:
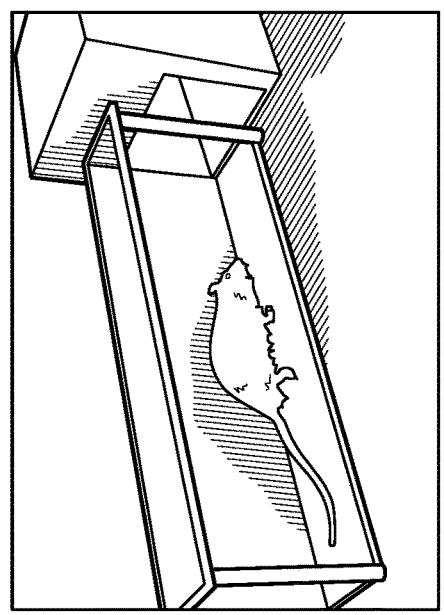
Figure 10B:
Figure 10A:
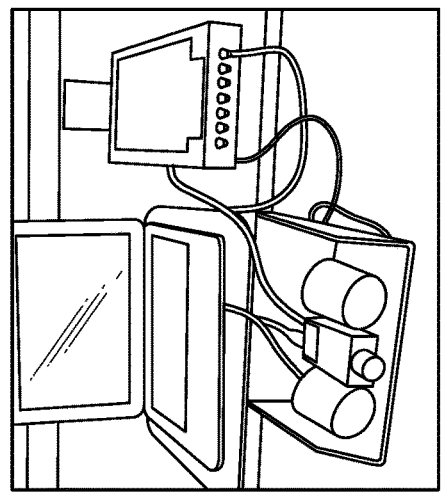

FIG. 10a shows a photo of high-speed camera with equipment for data acquisition used for recording videos of animal gait.

FIG. 10b shows a photo of anatomical placement of reflective markers for calculating joint angles during gait.

FIG. 10c shows a photo of a rat traversing walkway while being video recorded for gait analysis.

Figure 11:
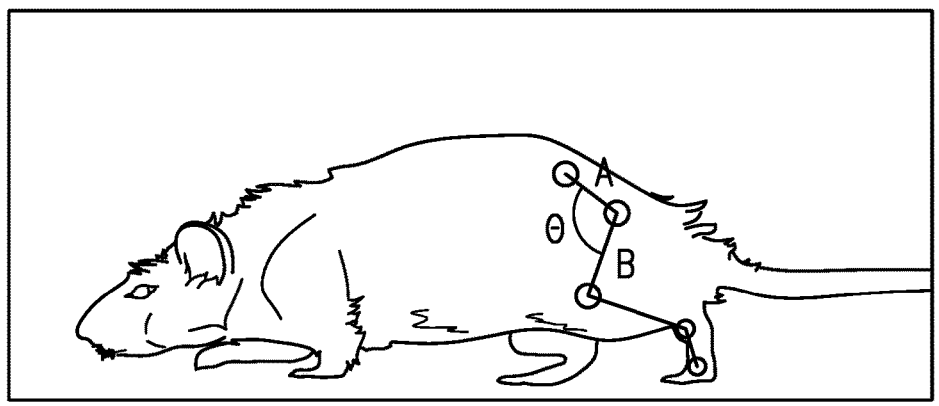

FIG. 11 shows an image of a rat captured during plantarflexion immediately before initiating the swing phase. Line segments connect each of the five reflective markers. Representative vectors indicated with A and B are used to calculate the intersegmental joint angle y. Color images available online at www.liebertonline.com/tea.

Figure 12A:
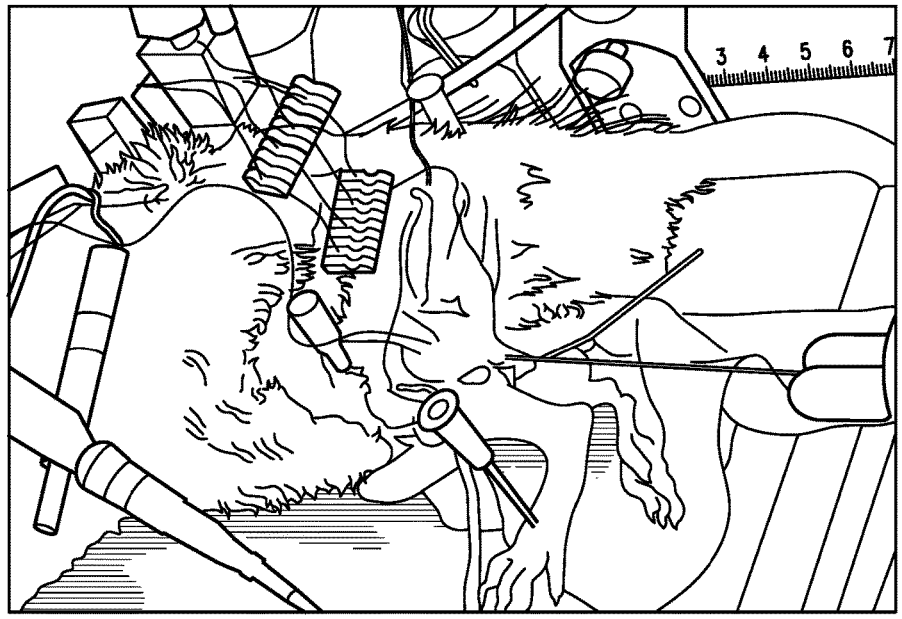
Figure 12B:
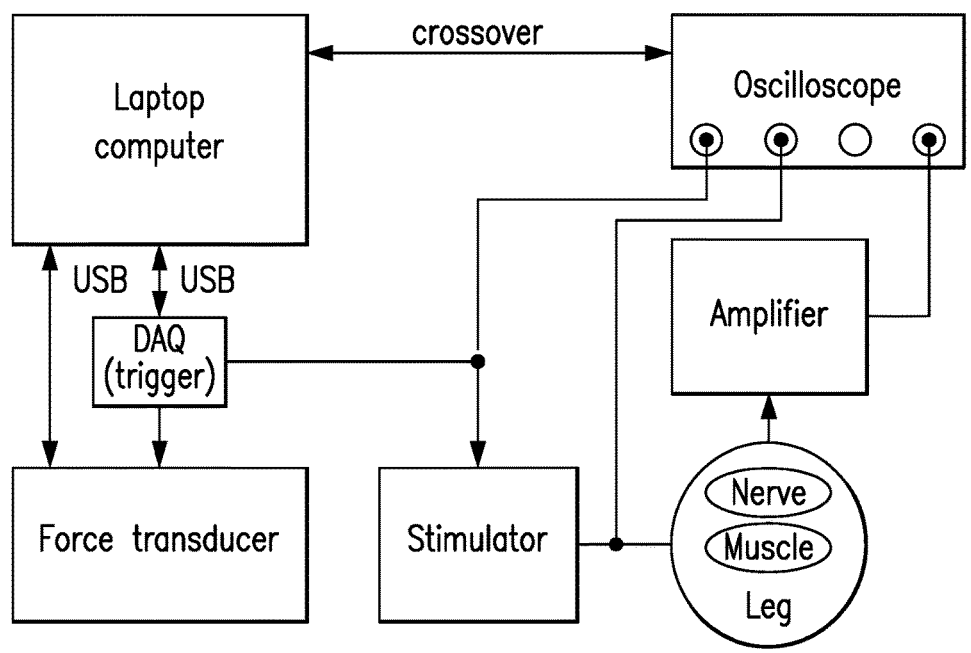

FIG. 12a shows a photo and FIG. 12b shows a schematic of a rat prepared on a data acquisition board for muscle contraction force recordings. Color images available online at www.liebertonline.com/tea.

Figure 13A:
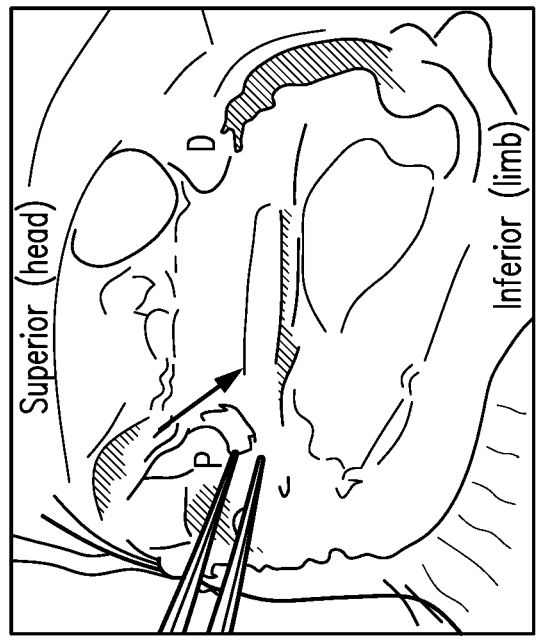

FIG. 13a shows a photo of exposed empty PCL nerve guide 16 weeks after implantation (white arrow). The proximal and distal ends of the guide are indicated with the characters P and D.

Figure 13B:
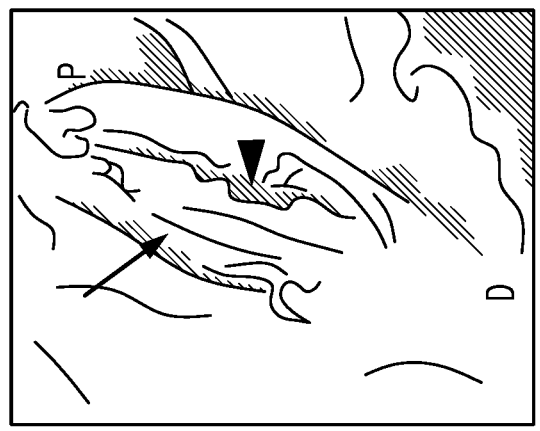
Figure 14A:
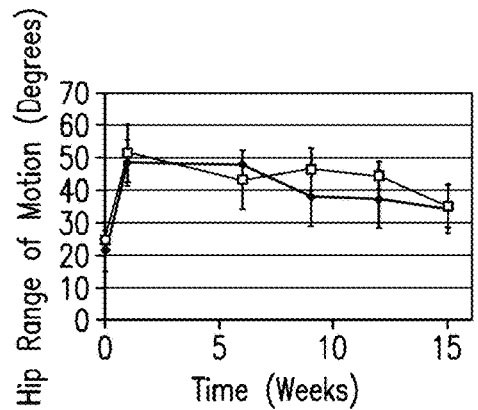
Figure 14B:
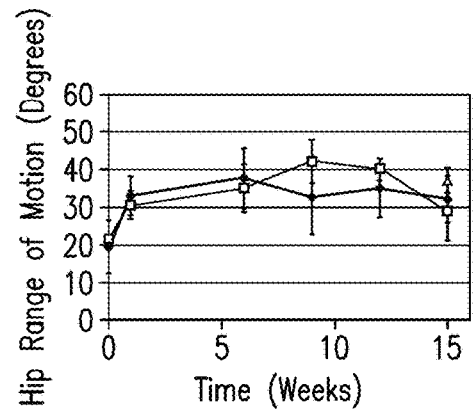
Figure 14C:
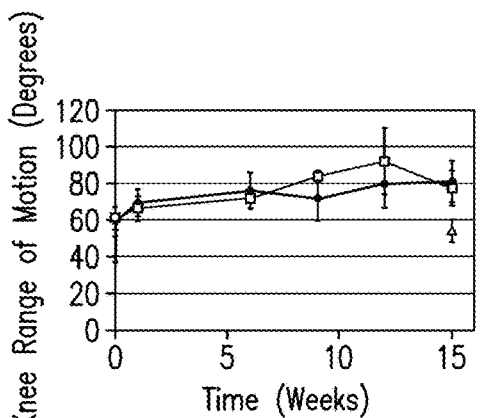
Figure 14D:
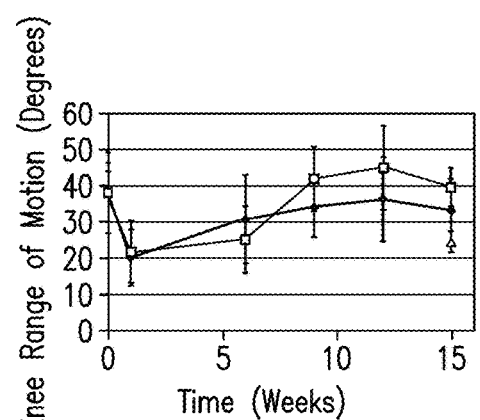
Figure 14E:
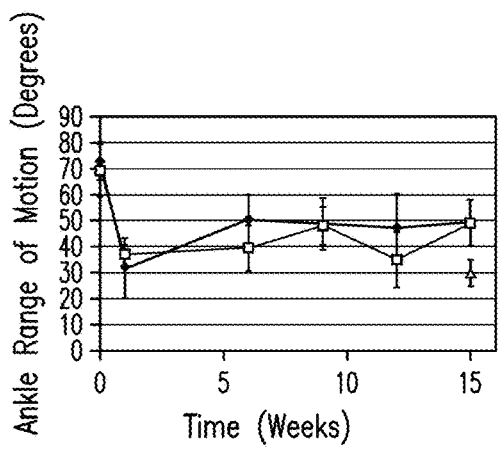
Figure 14F:
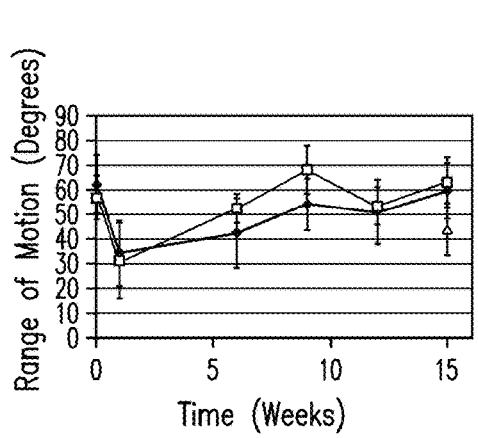

FIG. 13b shows a photo of GDNF releasing PCL nerve guide (white arrow) that has been longitudinally sectioned revealing regenerated nerve (white arrowhead). Color images available online at www.liebertonline.com/tea.

FIG. 14A-F shows hip range of motion (degrees) at baseline (week 0) and sequential timepoints after injury for swing phase (A) and stance phase (B) of the gait cycle. Knee range of motion during swing (C) and stance (D). Ankle range of motion (degrees) in swing (E) and stance (F). For all graphs, GDNF animals are represented with (♦), control PCL guides are (■) and isografts at week 15 are (▲).

Figure 15:
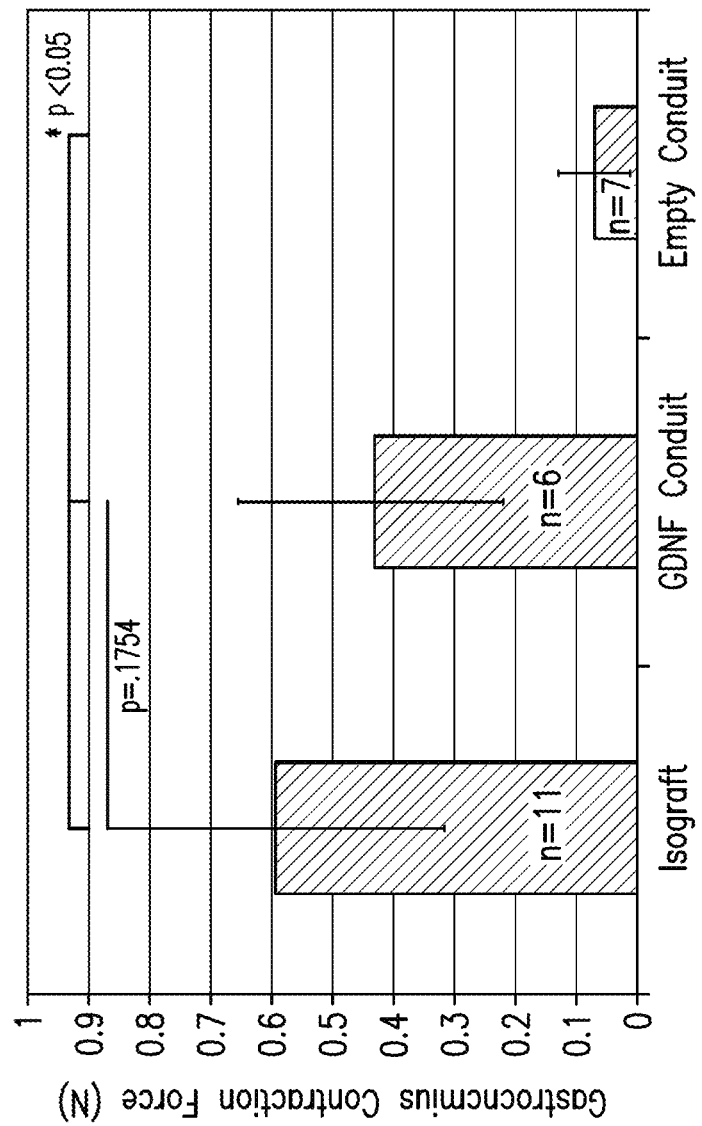

FIG. 15 shows the average gastrocnemius contraction force (N) with error bars representing standard deviation. *=p<0.05.

FIG. 16A-D shows transverse sections of the proximal segment of guides explanted after 16 weeks as observed with Masson's trichrome stain. (A) Low-magnification brightfield micrographs taken of negative control guides with regenerated nerve tissue indicated within black box. (B) High magnification micrographs showing detailed nerve tissue organization. (C) Low magnification transverse section from guides releasing GDNF with centrally located nerve tissue circled in black. (D) High magnification brightfield image of nerve fiber organization after GDNF treatment. Scale bars are 100 mm. NG¼ nerve guide. Color images available online at www.liebertonline.com/tea.

FIG. 17A-F shows transverse sections from guides explanted 16 weeks post injury observed with Masson's trichrome stain. Low magnification brightfield micrographs taken of negative control guides from the mid (A) and distal (B) sections of the explanted guide. (C) Low-magnification mid-transverse section from guides releasing. (D) High-magnification brightfield image of nerve fiber organization after GDNF treatment. (E) Low-magnification distal transverse section from guides releasing. (F) High-magnification brightfield image showing detail nerve fiber organization from within GDNF guides. Scale bars are 100 mm. Color images available online at www.liebertonline.com/tea.

FIG. 18A-F Fluorescent micrographs of proximal transverse sections of negative control guides (A) and guides releasing GDNF (B). Fluorescent micrograph from middle segment of control (C) and GDNF (D) nerve guides. Distal transverse section from negative control (E) and GDNF releasing nerve guides (F). Red indicates S100 labeling of Schwann cells. Neurofilament proteins within nerve fibers are green. 40,6-Diamidino-2-phenylindole is blue. Scale bars are 100 mm. Color images available online at www.liebertonline.com/tea.

Figure 19A:
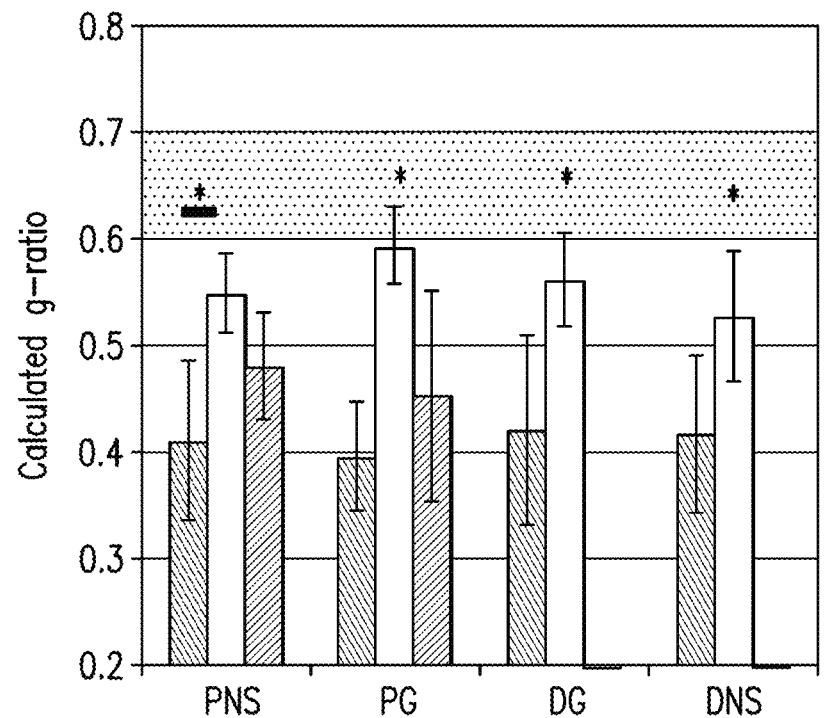
Figure 19B:
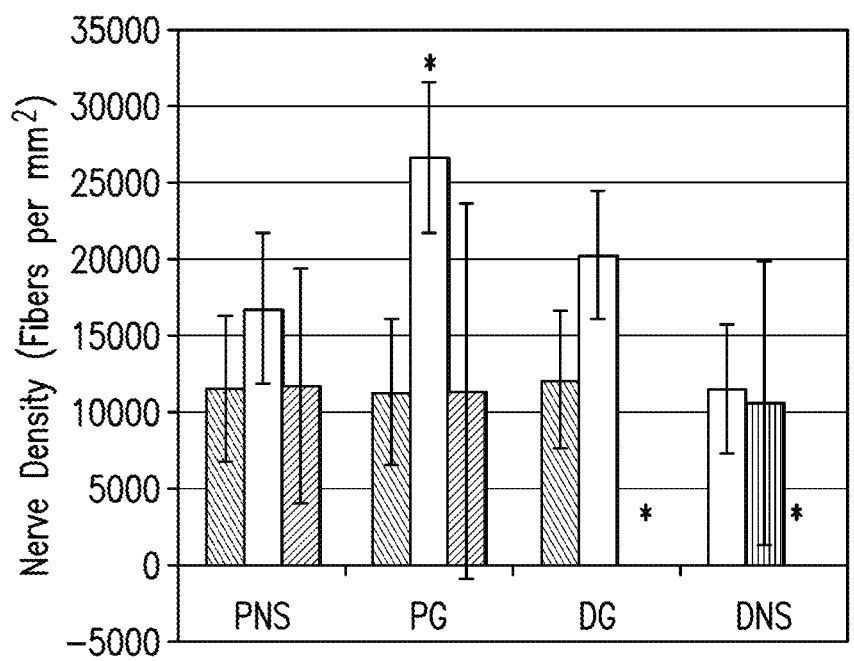

FIG. 19A-B. (A) shows calculated g-ratio of fibers within transverse segments of the PNS, PG, DG, and DNS. (B) Calculated nerve fiber density (fibers per mm2). Treatment groups are isograft (■), GDNF nerve guide (□) and control nerve guide (□). Values are expressed as mean|standard deviation. Gray horizontal bar indicates normal, uninjured g-ratio values. PNS, proximal nerve stump; PG, proximal graft or guide; DG, distal graft or guide; DNS, distal nerve stump. *=p<0.05.

5. DETAILED DESCRIPTION

A biodegradable polymer medical device having double-walled microspheres is provided that locally delivers an active agent (e.g., bioactive neurotrophic factor) in physiologically relevant concentrations for pre-selected periods (e.g. for at least 50 days). While the presently disclosed subject matter will be, for convenience, largely discussed with reference to a nerve guide, the presently disclosed subject matter is equally applicable to any medical device for which it is desired to deliver any active agent over an extended period of time. The device and/or microspheres of the invention may be used in a human, non-human primate, non-human mammal, rodent, or other non-human animal subject.

One embodiment of the presently disclosed subject matter provides a biodegradable polymer nerve guide that allows transected peripheral nerves to cross from a proximal to a distal nerve stump. Delivery of a neurotrophic factor enhances regeneration and overcomes current limitations in nerve repair across large defects. Glial Cell Line-Derived Neurotrophic Factor (GDNF) is a promoter of axonal elongation and branching and has shown promising pre-clinical results in analysis of nerve regeneration with nerve guides. In addition, GDNF has been shown to promote Schwann cell proliferation and migration. Other nerve factors that may be comprised in the microspheres include, but are not limited to, glial growth factor 2 (GGF2), brain-derived neurotrophic factor (BDNF), novel neurotrophin-1 (NNT1), Ciliary neurotrophic factor (CNTF), nerve growth factor (NGF), and neurotrophin-3 (NT-3). These agents, or a combination thereof, can be provided in addition to, or in place of, GDNF.

While the application has been described, solely for convenience, in the context of a nerve guide that employs a neurotrophic factor, the present invention encompasses other medical devices having double-walled microspheres containing active agent(s), where said microspheres are contained in a biodegradable polymer. Selection of the active agent can be made based on the function of the medical device, and the physiological needs of the subject to be treated. For example, and not by way of limitation, other agents that can be incorporated into double-walled microspheres include chemotherapeutic drugs (e.g., doxorubicin and/or cisplatin), insulin, dexamethasone, bone morphogenic protein-2, transforming growth factor β1, fibroblast growth factors 1 and 2, antihyperglycemic drugs (e.g., pioglitazone), kinase inhibitors, and combinations thereof.

Non-limiting examples of kinase inhibitors that may be incorporated into double-walled microspheres include glycogen synthase kinase 3 (GSK3) inhibitors such as SB-415286, LiCl, insulin-like growth factor-1, or SB216763, and agents set forth in: Cohen and Goedert, 2004, Nat. Rev. Drug Disc. 3(6): 479-487; Bhat et al., 2004, J. Neurochem. 89(6): 1313-1317; and MacAubay et al., 2003, Eur. J. Biochem. 270(18): 3829-3838; Rho/ROCK inhibitors such as fasudil or Y-27632 and agents set forth in Park, et al., 2011, J. Pharmacol. Exp. Ther. 338(1): 271-279; and Micuda et al., 2010, Curr. Cancer Drug Targets 10(2): 127-134; and JNK inhibitors such as SP600125 and "bidentate molecule 19" and agents set forth in Bogoyevitch and Arthur, 2008, Biochim. Biphys. Acta 1784(1): 76-93; Manning and Davis, 2003, Nat. Rev. Drug Discov. 2(7): 554-565; Stebbins et al., 2011, J. Med. Chem. PMID-21815634; and Bowes et al., 2011, Bioorg. Med. Chem. Lett. 21(18): 5521-5527.

In one embodiment, summarized in greater detail in the Examples below, a double-walled microsphere delivery system is provided for delivery of an active agent (e.g., bioactive GDNF) with a sustained release profile of at least 7 days, or at least 14 days, or in one preferred embodiment, at least 50 days. In this particular embodiment, microspheres, preferably double-walled microspheres, are incorporated within a degradable poly(caprolactone) nerve guide in a reproducible distribution. Implantation of nerve guides across a 1.5 cm defect in a rat sciatic nerve gap resulted in an increase in tissue integration in both the proximal and distal segments of the lumen of the nerve guide after 6 weeks. In addition, transverse sections of the distal region of the explanted guides showed the presence of Schwann cells while none were detectable in negative control guides. Migration of Schwann cells to double-walled microspheres indicated that bioactive GDNF was encapsulated and delivered to the internal environment of the nerve guide. Because GDNF increased tissue formation within the nerve guide lumen and also promoted the migration and proliferation of Schwann cells, the presently disclosed nerve guides can promote nerve regeneration beyond that capable with pre-existing nerve guides.

In one embodiment, double-walled microspheres including poly(lactide) and poly(lactic-co-glycolic acid) walls are incorporated into porous poly(caprolactone) nerve guides. The poly(lactide) wall can be the inner wall and the poly(lactic-co-glycolic acid) wall can be outer wall. Alternatively, the poly(lactide) wall can be the outer wall and the poly(lactic-co-glycolic acid) wall can be inner wall.

The order of the walls (that is to say, which polymer becomes the inner wall and which polymer becomes the outer wall) can be determined based on the principles of phase separation. For example, once solutions containing the two polymer "walls" are mixed to form an emulsion, the polymer layer that is first to precipitate out the solvent associated therewith (i.e. the solvent that is first to evaporate) will form the core layer, and the later-precipitating polymer will form the shell. Persons of ordinary skill in the art can obtain the desired wall order based on, for example, the hydrophilicity of the solvent selected, the polarity of the solvent selected, and the solubility profile of the polymer itself. Phase separation techniques are known to those of ordinary skill in the art, and details can be found, for example, in "In vitro and in vivo degradation of double-walled polymer microspheres," Journal of Controlled Release 40:169-178 (1996), and "In vitro degradation of polyanhydride/polyester core-shell double-walled microspheres," International Journal of Pharmaceutics, 301:294-303 (2005), each of which is hereby incorporated by reference in their entirety.

Bioactive proteins can be released from double-walled microspheres for over 80 days [21]. Double-walled microspheres can be reproducibly integrated within polymer nerve guides in manufacturer-controlled distribution. To confirm the distribution of microspheres within the nerve guide, fluorescently labeled bovine serum albumin (BSA) was encapsulated and visualized through fluorescent microscopy. Because particulate leaching is required to create the porous nerve guidewalls, the minimum period required for sodium chloride removal was determined. In vitro release studies were performed to determine the effect of the nerve guide macrostructure on release of a model protein, lysozyme. The overall efficacy of this fabrication technique was confirmed with GDNF in the rat sciatic nerve model. For evaluating the feasibility of the nerve guide design, a time period of only 6 weeks was used within the animal model. The rationale for this early time point was to first establish the bioactivity of proteins delivered within the lumen of the nerve guide from microspheres embedded within the nerve guide wall.

Results show that tissue integration within GDNF releasing nerve guides was improved with a greater concentration of intercellular fibers and collagen content. Furthermore, a localization of Schwann cells around microspheres encapsulating GDNF indicates that bioactive GDNF was being released from our delivery system.

While initial studies for evaluating nerve repair were conducted with a single growth factor, this technique could lend itself useful for evaluating delivery systems for additional growth factors or combinations thereof.

The presently disclosed subject matter also provides methods of making an implantable medical device (e.g., a nerve guide). In one embodiment, the method includes forming a first mixture (e.g., a solution) of a first polymer and a first solvent, and separately, forming a mixture (e.g., a solution) of a second polymer and a second solvent. The first or second polymer, which will ultimately form a wall of the double walled microsphere can be, for example, poly(l-lactide), poly(lactic-co-glycolic acid), poly(1,3-bis-(p-carboxyphenoxy propane)-co-(sebacic anhydride) (e.g., 20:80 PCPP:SA), poly(fumaric-co-sebacic) anhydride, and poly[(1,6-bis-carboxyphenoxy) hexane]. The first or second solvent can be, for example, water dichloromethane, ethyl acetate, diethyl ether, THF, acetone and EMSO.

For example, in an alternative embodiment, poly(lactic acid) can form the external layer and poly(1,3-bis-(p-carboxyphenoxy propane)-co-(sebacic anhydride) (e.g., 20:80 PCPP:SA) can form the core layer.

After a polymer is added to the mixture, and preferably after the polymer is fully dissolved, an active agent (e.g., GDNF) is then added to the first and/or second mixture. Alternatively, a component that is readily discernable (e.g., fluorescently-labeled bovine serum albumin) can be added in place of, or in addition to, the active agent for purposes of testing. Examples of active agents that can be added to the first and/or second mixture, and ultimately the medical device itself include neurotrophic factors, such as, but not limited to, glial cell-line derived neurotrophic factor (GDNF), brain-derived neurotrophic factor (BDNF), novel neurotrophin-1 (NNT1), Ciliary neurotrophic factor (CNTF), and neurotrophin-3 (NT-3). After adding the active agent, the mixture can be vortexed for a period of time (e.g., less than a minute) to achieve a homogenous mixture. An emulsifier such as docusate sodium salt can also be added to the first and/or second mixtures. An emulsifier, such as docusate sodium, or other stabilizer can be added to the first and/or second mixtures to stabilize the protein.

The two mixtures can then be combined, and optionally vortexed. When poly(lactide) and poly(lactic-co-glycolic acid) polymers are used as wall-forming polymers and dichloromethane is used as the solvent for the first two mixtures, an oil-in-oil emulsion is formed upon combining the two mixtures. The combined mixtures can be gradually added to a third solvent (e.g., drop-wise using a Pasteur pipette) to form a third mixture and then vigorously stirred for a few hours (e.g., stirred at 900 rpm for 3 hours). An aqueous solvent such as an aqueous solution of 0.5% poly(vinyl alcohol) can be used as the third solvent.

When polymer mixtures are combined to form the third mixture (e.g., an emulsion), the polymer that is associated with the solvent that is the first to evaporate will form the core of the microsphere, and the polymer that is associated with the solvent that is the last to evaporate will form the shell of the microsphere and at least substantially encapsulate the core polymer wall. In embodiments in which poly(lactide) and poly(lactic-co-glycolic acid) polymers are used as wall-forming polymers and dichloromethane is used as the solvent for the first two mixtures, the poly(lactic-co-glycolic acid) polymer will form the core layer, and the poly(lactide) will form the shell layer.

Microspheres are formed in the third mixture, which can be isolated, for example, by centrifugation and washing. For example, the third mixture can be centrifuged for about 10 minutes and washed with water, and then repeated. The microspheres obtained from the isolation step can then be lyophilized and stored at a low temperature in a desiccant.

Medical devices to which the double-walled microspheres are added, such as nerve guides can be prepared according to known methods. For example, double walled microspheres and nerve guides can be prepared as generally disclosed in Kokai et al., Diffusion of soluble factors through degradable polymer nerve guides: controlling manufacturing parameters, Acta Biomater 2009; 5(7):2540-50, which is hereby incorporated by reference.

In one embodiment, polycaprolactone nerve guides can be prepared by coating glass capillary mandrels with an aqueous polymer solution (e.g., a 17% w/v aqueous solution of poly(vinyl alcohol)). The coated capillary mandrels can then be introduced to a polymer slurry of polycaprolactone dissolved in an organic solvent (e.g., ethyl acetate) to which sodium chloride or other leaching salt has been added. The organic solvent is allowed to evaporate and the mandrel is again dipped in the polymer slurry. The resulting polymer conduits are immersed in distilled water, and the polymer subsequently removed from the glass mandrels. The thickness of the polymer nerve guide can be varied based on the number of immersions in the polymer slurry. For example, 6 immersions in polymer slurry yielded a nerve guide wall thickness of about 600-700 μm.

The double-walled microspheres can be added to the medical device by introducing the microspheres to the medical device in between immersions in the polymer slurries. For example, the semi-dried, dip-coated medical device can be introduced to microspheres that are even spread across a non-reactive surface (for example, but now by way of limitation, parchment paper) by rolling, or by similar means, and allowed to dry before subsequent dip-coating. Any technique can be used to apply the microspheres to the biodegradable, yet otherwise inert polymer (e.g. polycaprolactone) so long as the process does not dissolve or otherwise negatively impact the microspheres. For example, processes requiring high temperatures should be disfavored, unless the microspheres can be protected. Electrospinning and polymer casting techniques known to those of ordinary skill in the art can be used.

The present invention further provides for, but is not limited to, nerve guides prepared by the method set forth above.

6. EXAMPLE: INCORPORATION OF DOUBLE-WALLED MICROSPHERES INTO POLYMER NERVE GUIDES

6.1 Materials and Methods

Reagents:

All chemicals were analytical grade or purer and were purchased from commercial suppliers. Poly(vinyl alcohol) (average Mw 9000-10,000, 80% hydrolyzed), poly(DL-lactide-co-glycolide) (lactide:glycolide (50:50), mol wt 40,000-75,000 units), poly(caprolactone) (Mw 65,000), Fluorescein isothiocyanate conjugated Bovine Albumin (A9771) (FITC-BSA), lysozyme from chicken egg white, dichloromethane, ethyl acetate, Gel Mount (G0918), xylene, monoclonal anti-S100, and Phosphate Buffered Saline (PBS) were all purchased from Sigma-Aldrich (St. Louis, Mo.). Poly-L-lactide (0.90-1.20 dL/g) was purchased from DURECT Corporation (Pelham, Ala.). The Micro Bicinchoninic Acid (BCA) Protein Assay Kit (23235) was purchased from Pierce (Rockford, Ill.). The Masson's trichrome kit was purchased from American MasterTech (Modesto, Calif.). The GDNF Emax Immuno-Assay Systems Kit was purchased from Promega (Madison, Wis.). Recombinant human Glial-Derived Neurotrophic factor (GDNF) produced in *E. Coli* was purchased from Leinco Technologies (St. Louis, Mo.).

Fabrication of Double-Walled Microspheres:

To create double-walled microspheres, a 17.5% poly (lactic-co-glycolic acid) (PLGA) solution was created with 150 mg PLGA in dichloromethane. In a separate glass scintillation vial, a 10% solution of poly(lactide) (PLLA) of equal polymer mass was prepared. After both polymers were fully dissolved, either 4 mg of FITC-BSA or 20 mg of lysozyme was added to the PLGA solution and vortexed for ~30 s to achieve a homogenous mixture. The PLGA solution was then combined with the PLA solution and vortexed for an additional 60 s. This oil-in-oil emulsion was added drop-wise through a Pasteur pipette to 200 mL of aqueous 0.5% poly(vinyl alcohol) solution stirring at 900 rpm for 3 h. Then, the polymer microspheres were collected through centrifugation (1500 g for 10 min) and washed three times. Finally, the microspheres were lyophilized using a Labconco freeze dry system (without a cryoprotectant) and stored in a desiccant at ~20° C.

To encapsulate glial cell line-derived neurotrophic factor (GDNF), a solution of 40 ml (0.1 mg/mL) of GDNF, 100 mg of docusate sodium salt and 7 mg human serum albumin was prepared in 0.5 mL sterile water over ice (formulation adapted from [22]). After mixing well, the solution was frozen and lyophilized. The protein/surfactant mixture was then added to PLGA already dissolved in dichloromethane and microspheres were prepared, as described for lysozyme encapsulation.

GDNF Release from Double-Walled Microspheres:

To determine the release kinetics of GDNF from the PLGA/PLA double-walled microspheres, 10 mg of microspheres were placed into Eppendorf tubes and incubated in 1 mL PBS at 37° C. At specified time points, the microspheres were vortexed, centrifuged for 10 min at 1500 g and the supernatant was replaced with fresh PBS. The amount of soluble GDNF in the collected samples was analyzed using an enzyme linked immunosorbent assay (ELISA) manufacturer's instructions. The optical density was recorded at 450 nm in an ELISA plate reader (Tecan, N.C.). The GDNF concentrations were calculated against a 6-point standard curve, then adjusted to picograms of GDNF per milligram of microspheres.

Figure 1A:
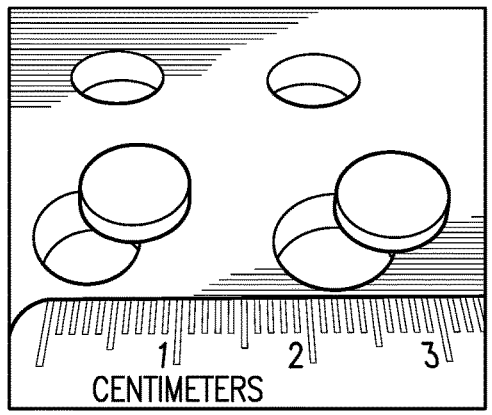
FIG. 1a is a photograph of PCL disks following fabrication in custom made silicone mold.

Fabrication of Poly(Caprolactone) Disks and Nerve Guides:

Poly(caprolactone) (PCL) disks were prepared to determine the effect of nerve guide macrostructure on lysozyme release from the microspheres. Briefly, 15 mg of microspheres were added to a circular well (diameter=1 cm, depth=0.5 cm) of a custom made silicone mold (FIG. 1A). Porous disks were created by dissolving 1.35 g PCL in 15 mL ethyl acetate. To the dissolved polymer solution, sodium chloride impregnation was accomplished by adding NaCl in a 80% (v/v) amount. 200 ml of the polymer slurry was added to each mold and mixed well to distribute the microspheres within the disk space. The ethyl acetate was allowed to evaporate and the sodium chloride was leached with distilled water.

PCL nerve guides were fabricated using a modification of previously reported methods [23]. Glass capillary mandrels 1.5 mm in diameter were coated with a 17% w/v % aqueous solution of poly(vinyl alcohol) (PVA), air dried and then immersed into the polymer slurry (as described above) creating NaCl/PCL mandrel coatings. The ethyl acetate was allowed to evaporate for a minimum of 10 min between successive mandrel immersions into the polymer slurry. After the completion of the dip-coating process, the resulting polymer conduits were submerged in distilled water to allow for salt and PVA dissolution, and the guides were removed from the glass mandrels. The final wall thickness after 6 successive immersions of the mandrels into the polymer solutions was 600-700 mms.

Figure 1B:
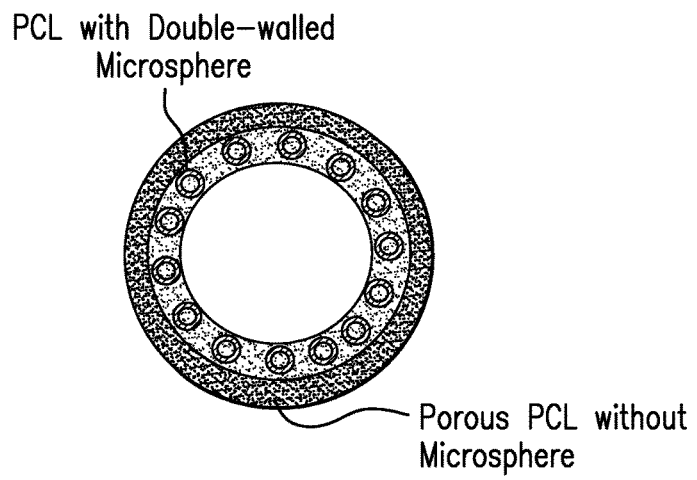
FIG. 1b is a schematic of polymer orientation in double-walled microsphere.
Figure 1C:
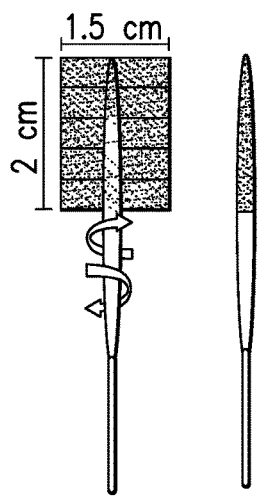
FIG. 1c is a schematic of a fabrication technique for incorporating double-walled microspheres into PCL nerve guide.

To incorporate double-walled microspheres into the inner half of the nerve guide wall (FIG. 1B), 15 mg of microspheres were evenly spread onto a drawn grid on parchment paper (FIG. 1C). After the first immersion of the glass mandrel into the PCL slurry, the ethyl acetate was allowed to evaporate for only 30 s leaving a semihardened polymer layer on the mandrel. This was then smoothly rolled across the microspheres on parchment paper. The PCL with embedded microspheres was allowed to dry for 10 min and then repeatedly coated with additional layers of polymer as done in nerve guides without microspheres.

Evaluation of Sodium Chloride Leaching from Nerve Guide Walls:

To determine the minimum amount of time required to leach the sodium chloride from the nerve guide walls, nerve guides were fabricated as described above (n=5). After ethyl acetate evaporation overnight, each mandrel with the attached polymer guide was weighed. The mandrels were then immersed in distilled water in 1 h increments. The dry weight of each guide was recorded between successive salt leaching periods. Previous work has indicated that in an 80% porous nerve guide, very few closed pores exist from which remaining salt crystals could not dissolve [23].

Visualization of Microsphere Distribution within Nerve Guides:

To assess the distribution of microspheres within PCL nerve guide walls, nerve guides with embedded microspheres encapsulating FITC-BSA were submerged in Optimal Cutting Temperature (O.C.T.) compound and frozen for sectioning with a cryostat. The nerve guides were then sectioned (15 mm) and either fixed onto glass slides or mounted on metal stubs using double-sided copper tape. The overall location of microspheres within nerve guides was then evaluated using low magnification (10×) fluorescent microscopy. To determine the effect of the nerve guide fabrication process on microsphere morphology, high magnification scanning electron microscopy was performed. Transverse sections of nerve guides mounted on metal stubs were coated with gold using a Cressington 108 Auto (Cressington, Watford UK) and then viewed with a JEM-6330F (JEOL, Peabody, Mass.) scanning electron microscope operating at 5 kV acceleration.

In Vitro Release of Lysozyme from Poly(Caprolactone) Disks and Nerve Guides:

To determine the effect of the nerve guide material on lysozyme release from double-walled microspheres, protein release kinetics were compared between a known weight of microspheres embedded in PCL disks to an equal weight of free microspheres in solution. To accomplish this, 15 mg of microspheres were first immersed in water for a period identical to that used to remove the salt particulates from the PCL disks. The microspheres were then collected and incubated in 1 mL PBS at 37° C. Following incubation, the microspheres were centrifuged for 10 min at 1500 g and the supernatant was removed. Five PCL disks prepared as described above were individually placed into wells of a 48 well plate. To each disk, 0.6 mL of PBS solution was added and the well plate was incubated for equal time periods as microsphere samples. To collect the releasate, the disks were removed using sterile forceps and transferred into clean wells where the PBS was refreshed. To measure the release of lysozyme from double-walled microspheres in PCL nerve guides, nerve guides were fabricated as described in Section 4.2. After the guides were immersed in distilled water for 5 h, the guides were cut to 2 cm lengths and added to a clean Eppendorf tube. To each tube, 0.6 mL of PBS was added and the guides were incubated at 37° C. for specified time increments. To collect the releasate, the guides were removed from each Eppendorf tube using clean forceps and added to new tubes in which the PBS was refreshed.

For measuring the lysozyme content of the releasate, a micro BCA protein analysis assay was performed. Lysozyme standard or sample solution (1 mL) and 1 mL of the Micro BCA working reagent were combined in a test tube and mixed well. All of the standard lysozyme samples as well as the release samples were incubated simultaneously in a water bath for 1 h at 60° C. After this period, the protein solutions were cooled to room temperature and 200 mL from each sample were transferred to a 48 well plate and read with a plate reader at 562 nm (Tecan Spectraflour, N.C.).

Surgical Methods:

Following the guidelines of the University of Pittsburgh Institutional of Animal Care and Use Committee, 6 male Lewis rats (250-300 g, Harlan Labs) were used to evaluate the initial efficacy of GDNF released from PCL nerve guides for improved nerve regeneration. To implant the guide, each rat was anesthetized with an intraperitoneal injection of sodium pentobarbital (50 mg/kg). The sciatic nerve was then exposed with a muscle splitting incision of the gluteal muscle. The nerve was sharply transected ~0.5 cm from the proximal bifurcation and 0.5 cm of tissue was excised. After the proximal and distal nerve stumps were allowed to retract, the exposed fascicles were trimmed and sutured with 10-0 prolene epineurial mattress stitch 1 mm into each end of a 1.7 cm nerve guide, creating a 1.5 cm defect (FIG. 2A). The gluteal muscle and skin were then closed with 4-0 vicryl suture. The animals were randomly divided evenly amongst two groups, one of which received conduits with microspheres encapsulating GDNF and the other group received identical conduits with empty microspheres as a negative control.

Histological Analysis:

After 6 weeks, the animals were sacrificed with an overdose of sodium pentobarbital and the implanted guides were harvested and immediately fixed in 4% paraformaldehyde. After the tissue was fixed for at least 24 h, the nerve samples were washed with PBS and fixed in 1% osmium tetroxide for at least 2 h. After the nerve specimens were dehydrated with increasing concentrations of ethanol (30-100%), the nerves were sectioned with a sharp razor blade at the proximal nerve stump (PS), the proximal (PG), middle (MG) and distal (DG) regions of the nerve conduit, and at the distal nerve stump (DS) (FIG. 2). The sections were then embedded in paraffin in descending order (FIG. 2C) and sectioned at 3 mm in thickness.

Masson's Trichrome:

For analysis of cellular and tissue infiltration of the nerve conduits, nerve sections from the negative control and experimental animals were stained for Masson's Trichrome. Sectioned nerves were first deparaffinized with xylene and rehydrated with decreasing percent alcohol solutions (100% followed by 90% and then DI water). Solutions from a Masson's trichrome kit were then used according to the protocol published by Di Scipio et al. [24].

Immunohistochemistry:

For fluorescent visualization of Schwann cells, immunohistochemistry was performed on explanted nerve samples. Paraffin embedded specimens fixed in osmium tetroxide were first deparaffinized as described above and then etched with $H_2O_2$ for 10 min as described in [24]. The samples were then blocked with 5% FBS with 0.02% triton-X in PBS for 1 h at room temperature. Antibodies against S-100 protein were then added overnight at 4° C. (1:400 in 2.5% FBS and 0.02% triton-X in PBS). The samples were then washed three times with PBS and the secondary antibody was added for 1 h at room temperature (1:1000 in 2.5% FBS and 0.02% triton-X in PBS). The samples were then washed thrice again and the nuclei were detected using DAPI (0.6 mg/mL). The slides were then mounted with a fluorescent mounting media.

Statistical Analysis:

A minimum repetition value of five was used when measuring lysozyme release from PCL disks and nerve guides. Results are expressed as the mean±standard deviation. Analysis of variance (ANOVA) was used to determine statistical significance between experimental groups. The least significant difference method was used for multiple comparisons with p<0.05.

6.2 Results

Growth Factor Release from Double-Walled Microspheres:

Microspheres were prepared encapsulating fluorescently labeled BSA for protein visualization, lysozyme to characterize protein release from microspheres embedded in PCL, and a neurotrophic factor: GDNF. The microspheres batch yield was 54.5%. GDNF release from double walled microspheres was determined using ELISA. The release profile indicates an initial burst release of GDNF during the first day of microsphere incubation, with 4.8±0.4 ng GDNF measured per mg microspheres (FIG. 3A). Following the initial burst, GDNF was released with near zero-order kinetics and by day 64 had a cumulative release of 6.4±0.02 ng GDNF per mg microspheres. The overall percent bioactivity of GDNF released from microspheres alone was not assessed in vitro. Instead, GDNF integrity (bioactivity) was evaluated from the overall nerve guide delivery system in vivo. Because we incorporated 15 mg of microspheres into each guide, we approximate the GDNF dosage during in vivo studies as ~95 ng per animal. The cumulative release of the GDNF (pg) per individual nerve guide (1.7 cm in length) is depicted in FIG. 3C, with values expressed as mean±std. dev. (n=4).

Minimization of Salt Leaching Period:

Leaching of sodium chloride from the nerve guide walls also results in a loss of protein from the microspheres. Therefore, it is desirable to minimize the immersion of nerve guides in water. Following fabrication of PCL nerve guides impregnated sodium chloride, the PCL guides were immersed in distilled water for 1 h increments. FIG. 3B indicates that the majority (97%) of NaCl was removed from the nerve guide wall after 1 h of immersion in water. Beyond 5 h, no amount of measurable NaCl was further removed.

To validate the final PCL nerve guide weight, the guides were weighed after 60 h of immersion in water and the final weight was unchanged. Because the initial weight of NaCl within nerve guides cannot be accurately measured (guides are made by dipping mandrels in a large volume of polymer/salt slurry), it is assumed here that only a negligible amount of NaCl remains within closed pores following the extended period of mandrel immersion in water. This assumption is supported by the very low frequency of closed pores detected in 80% porous PCL nerve guides [23].

Incorporation of Double-Walled Microspheres into Nerve Guides:

A novel rolling technique was used to embed double-walled microspheres into PCL nerve guides for sustained protein release. Fluorescently labeled BSA was encapsulated in the double-walled microsphere to visualize microsphere distribution within the nerve guide wall. Fluorescent microscopy images were then taken of the microspheres and overlaid with light microscopy images of the polymer nerve guide. As seen in FIG. 4A, by smoothly rolling the nerve guide mandrel across the microspheres and performing several consecutive immersions of the mandrel into the polymer solution, a nerve guide was created with microspheres distributed evenly along the luminal wall of the nerve guide. Because PLA is not soluble in ethyl acetate, the rounded morphology of the microspheres was maintained following nerve guide fabrication (FIG. 4B).

Lysozyme Release from Double-Walled Microspheres Embedded in Poly(Caprolactone):

A known weight of double-walled microspheres was incorporated into PCL disks to measure the effects of nerve guide macrostructure on protein release. Lysozyme was released from microspheres in a significantly higher concentration than from microspheres embedded in PCL (p<0.05, n=5). The cumulative amount of protein released at day 35 was not significantly different between free floating microspheres and microspheres in disks (p>0.05) (FIG. 5A). To analyze the long-term release of protein from PCL nerve guides, 15 mg of double-walled microspheres identical to those used in the disks were embedded into the walls of 5 individually prepared nerve guides. The lysozyme release pattern seen from nerve guides was similar to that seen from microspheres alone (FIG. 5B). There was a gradual, sustained release of lysozyme until day 36 when ~45% of the total lysozyme was released. After this period, there was an increase in release rate and by day 49, 90% of lysozyme was released. No detectable amount of lysozyme was measured beyond day 56. As a BCA assay was used to detect lysozyme in solution, even partially degraded protein fragments would still be detected. Therefore, the remaining 10% of encapsulated lysozyme had most likely adsorbed onto the remaining polymer matrix of microspheres.

Masson's Trichrome:

PCL nerve guides with double-walled microspheres were implanted across a 1.5 cm defect in the sciatic nerve to determine the initial effects of GDNF delivery on nerve regeneration. The presence of cellular infiltration, tissue formation and collagen content within the implanted conduits was visualized through Masson's trichrome stain. At low magnification (FIG. 6A), transverse images of proximal segments of PCL conduits implanted without encapsulated GDNF showed a thin collagen capsule surrounding the nerve guide (arrow). Within the lumen of the guide, there is incomplete tissue integration and a lack of intercellular fibers. High magnification images (FIG. 6B) reveal the presence of blood vessels (arrow head) and localization of cells near the inner surface of the nerve guide. There does not appear to be a measurable number of nerve fibers present and the majority of infiltrating cells, such as fibroblasts and macrophages, are organized around the nerve guide wall and surround the microspheres (MS). Neither the experimental nor control guide appear to illicit a strong inflammatory response.

Visualization of nerve guides implanted with double-walled microspheres releasing GDNF shows a higher concentration of intercellular fibers and tissue formation at the proximal segment of the guide (FIG. 6C). Though connective tissue does not appear to be organized, high magnification images of the center of the nerve guide reveal the presence of cells throughout the entire interior of the guide (FIG. 6D). The presence of a blood vessel located near a microsphere in the nerve guide wall is indicated with an arrow head. In the distal region of the implanted nerve guides, the empty conduit shows very little tissue formation in the lumen of the guide in comparison to guides releasing GDNF (FIGS. 7A and B). Analysis of high magnification light micrograph images confirmed that in negative control guides, there is an absence of intercellular fibers and cells in the lumen of the guide (FIG. 7C). In GDNF conduits (FIG. 7D), tissue infiltration is not as developed as was seen in the same proximal nerve segment, however there was an increase in collagen content and intercellular fibers above the negative controls.

Immunohistochemistry:

Results from immunohistochemical analysis of nerve sections treated with anti-S100 antibodies showed that Schwann cells were present in the proximal nerve guide segment in both negative control and nerves that received guides with GDNF microspheres. However, as seen in FIG. 8A, the distribution of Schwann cells in control guides was largely restricted to the middle of the nerve guide. Within the lumen of nerve guides releasing GDNF, Schwann cells are evident not only in the center of the conduit, but also surrounding the microspheres (FIG. 8B). At higher magnification, Schwann cells (red) are visualized surrounding the double-walled microspheres releasing GDNF (FIG. 8D) but are not present around non-encapsulating control microspheres (FIG. 8C). Analysis of the distal regions of the explanted nerve guide reveals the presence of Schwann cells in the lumen of only those guides releasing GDNF. In FIG. 9A, DAPI staining of nuclei reveals the presence of unspecified cells in smaller number in control guides as compared to GDNF guides (FIG. 9B). Also evident in FIG. 9B is a small population of Schwann cells is present in the experimental guides not seen in the negative control guides.

6.3 Discussion

Direct bolus application of neurotrophic factors is not a suitable method for determining the long term effect of such molecules on nerve regeneration due to the short half life of growth factors in vivo. Therefore, it is desirable to use a controlled growth factor delivery system that is capable of delivering neurotrophins to Schwann cells and nerve stumps at the site of ligation in the sciatic nerve over a sustained period. To accomplish this, we looked toward traditional microsphere drug delivery systems as a method of encapsulating a neurotrophic factor. Typical microsphere release kinetics include an initial burst of protein release within the first 24 h of placement in aqueous solution either in vitro or in vivo. To increase the time over which protein is released, PLGA microspheres were coated with an additional layer of polymer (e.g. PLA), creating a double-walled microsphere. With this technique, the encapsulated growth factor is protected in the core of the two-layered core-shell microsphere structure. Furthermore, by localizing a growth factor to the core of the double-walled microsphere, the amount of material through which the protein must diffuse through is increased thus slowing the protein release rate. In addition, double-walled microspheres with a core of PLGA and a poly(L-lactide) (PLA) shell is an effective method of incorporating the microspheres into PCL nerve guide walls. PLA is not soluble in ethyl acetate, the solvent used to create the PCL/NaCl slurry for nerve guide fabrication and therefore protects the microspheres from dissolution during nerve guide fabrication.

In the present study, it has been demonstrated that GDNF can be encapsulated at a concentration measuring several nanograms per milligram of double-walled microspheres. The microspheres were reproducibly incorporated into PCL nerve guides in a distribution that was tailored to manufacturer specifications. Lysozyme release studies from microspheres embedded in PCL disks suggest that the nerve guide material delays the initial release of protein into the aqueous environment, presumably because the protein is trapped within the porous architecture of the nerve guide wall. In the creation of our PCL nerve guides, it was initially hypothesized that this effect of nerve guide macrostructure on the initial protein release kinetics would be of benefit for our application, as the initial burst of GDNF from the microspheres (FIG. 3A) would be delayed and closer to zero-order. However, lysozyme release from the double-walled microspheres within nerve guide walls was no longer detectable after 54 days while previous work in our lab has shown that microspheres suspended in PBS release protein for >80 days [21]. It is possible that released protein adsorbs to the PCL surface upon release and is entrapped within the nerve guide wall. Initial exposure of the PCL guide surface to blood proteins following implantation in vivo would likely minimize GDNF adsorption upon release from microspheres.

While the benefits of many different neurotrophic factors have been assessed in sciatic nerve defects (e.g. NGF, BDNF, CNTF) we chose to initially implant nerve guides releasing GDNF because of the promising results described in literature. GDNF is a neuroprotective growth factor secreted by Schwann cells in distal segments of peripheral nerves following injury [25]. In addition, GDNF has been shown to prevent avulsion-induced motor neuron death following complete nerve transection whereas nerve growth factor (NGF), brain-derived neurotrophic factor (BDNF), and insulin-like growth factor (IGF) all failed to enhance cell survival or cell size [26]. Finally, GDNF treatment with guidance channels following spinal cord injury resulted in a reduction of reactive astrocytosis and macrophage accumulation [27]. The efficacy of GDNF toward improving peripheral nerve regeneration through nerve guidance conduits has also been evaluated in vivo. In a 2007 study by Patel et al., chitosan scaffolds blended with laminin-1 and 5 mg GDNF were implanted across a 10 mm gap in the Lewis rat sciatic nerve [28]. After 12 weeks, the chitosan/GDNF guides resulted in decreased gastrocnemius muscle atrophy and restoration of functional strength that was comparable to autograft controls. Behavioral testing indicated GDNF treatment groups regained sensation and improved gait kinematics. In addition, silicone conduits filled with GDNF gene modified Schwann cells have resulted in significantly improved nerve conduction velocity, number and density of regenerated nerves, and the thickness of themyelin sheath of regenerated nerves than that seen in controls across a 10 mm defect in the Wistar rat [29]. Finally, nerve guides with a GDNF releasing rod increased the number of myelinated axons and the overall number of regenerated axons was four-fold higher than nerve guides with NGF [7].

Within published literature concerning growth factor delivery from nerve guides, there is a wide range of target growth factor dosage. This variability could reflect the particular therapeutic index, half-life, or delivery method for each growth factor. For example, Lewin et al., investigated the effect of brain-derived neurotrophic factor (BDNF) and Ciliary neurotrophic factor (CNTF) on peripheral nerve transections through the delivery of 300 mg of each growth factor via osmotic pump (delivering approximately 9 mg/day) [18]. Lower dosages of nerve growth factor (NGF) have been used within heparin-containing silicone nerve guides, with tested dosages of 5, 20 or 50 ng NGF/mL [16]. Additionally, while in vitro models using dorsal root ganglion explants have been used to predict optimal growth factor combinations for axonal outgrowth [30], it is difficult to predict optimal dosages for implantation considering the increased complexity of an in vivo environment. Therefore, we did not intend to deliver an optimal concentration of GDNF within this preliminary nerve guide delivery system feasibility study. Instead, we established the highest weight of microspheres which could be embedded within the nerve guides reproducibly, or 15 mg microspheres per 1.7 mm long nerve guide. Upon establishing the efficacy of this nerve guide model it will be possible to adjust microsphere formulations for improved encapsulation efficiency or to vary the weight of microspheres embedded within the nerve guide walls for establishing an ideal dose of growth factor.

Our in vitro release studies suggest that GDNF was released continuously during the 6 week period of guide implantation across the sciatic nerve lesion. While nerve gaps treated with empty microsphere conduits resulted in incomplete fibrotic tissue formation and scattered fibroblast-like cells in the center of proximal segment of the excised nerve guides, nerve guides releasing growth factor reveal an increase in cellular infiltration and tissue integration within the lumen of the conduits. In addition, tissue integration in the distal segments of nerve guides was markedly improved in guides releasing GDNF. High magnification micrographs of the central portion of transverse segments (FIGS. 7B and C) reveal an overall increase in cellular infiltration and collagen content following GDNF treatment. This increase in collagen content could potentially supply an improved scaffold for Schwann cell migration and support axonal outgrowth.

Detection of Schwann cell localization with immunofluorescence indicated that Schwann cells were present in proximal segments of PCL nerve guides. Fluorescent micrographs of control guides show a significant number of Schwann cells within the lumen of the guide (FIG. 8A) and Schwann cells do not appear to localize to the conduit wall or microspheres (FIG. 8C). Nuclear staining (DAPI) within the conduit center reveal a large presence of additional cell populations which most likely include fibroblasts and macrophages but were not positive for antibodies against neurofilament antibodies (FIG. 8C). However, micrographs of nerve guides with GDNF microspheres show a population of Schwann cells encircling the microspheres, an indication of targeted migration of Schwann cells toward a source of GDNF (FIGS. 8B and D). This result is significant for two reasons. First, a cellular response to the encapsulated growth factor suggests that the released GDNF is bioactive and has not been completely denatured through the nerve guide fabrication process. Second, the migration of Schwann cells, presumably from the lumen of the conduit, indicates that GDNF is being delivered to the lumen of the nerve guide in a physiologically relevant concentration and is not entirely entrapped within the porous nerve guide structure.

Nerve guides encapsulating GDNF also resulted in the presence of Schwann cells at the distal portion of transverse sections of explanted tissue that was not seen in control guides (FIGS. 9A and B). Fluorescent micrographs of the central portion of the nerve guide reveal an increase in both cellular infiltration (DAPI) and cells positive for antibodies against S-100 protein in experimental guides while there were no detectable positive for S-100 in control guides. The presence of Schwann cells in the distal segment of experimental nerve guides could be a result of either Schwann cell proliferation or migration. Though GDNF is typically utilized in nerve regeneration as trophic factor for nerve fibers and as a promoter of axonal growth [31] and branching [32, 33], GDNF also causes a marked proliferation and migration of Schwann cells [33, 34]. The effect of GDNF is RET (receptor tyrosine kinase) independent and instead, GDNF signaling mechanisms directly in Schwann cells through a GPI-anchored coreceptor (GFR-a1) and neural cell adhesion molecule (NCAM)[34]. Additionally, downstream signaling protein kinases (PKA) participates in GDNF transcription, and therefore, GDNF promotes a positive feedback loop for autocrine signaling in Schwann cells. This autocrine feedback loop has been reported to further enhance Schwann cell migration and myelination [25], both of which are important events in nerve regeneration.

The presence of regenerated nerves into nerve stumps distal to the implanted conduits was not assessed due to the early time point used within this study. The intended purpose of this study was to establish the feasibility of our overall nerve guide design for delivering bioactive proteins to injured peripheral nerves from degradable polymer conduits. It was our hypothesis that an early time point would improve the likelihood of observing a distinct cellular response within conduits which deliver growth factor and the negative control guides. Furthermore, because we did not anticipate nerve regeneration to have been completed across the large gap used within our animal model, we did not look for functional recovery of lower leg muscle as they would not yet be properly innervated. Following the completion of this preliminary study, a longer time point will be used in future studies which aim to determine the efficacy of our selected growth factor, GDNF, for improving nerve regeneration.

Double-walled microspheres were fabricated as a method of encapsulating GDNF, and subsequently incorporated into biodegradable polymeric nerve guides. Initial in vitro release studies from microspheres reveal a sustained release of GDNF to day 50, a time point beyond our 6 week implantation period. An analysis of the effects of the nerve guide material, PCL, on release kinetics from incorporated microspheres revealed that porous PCL delayed the initial period of protein release until day 35, when no significant difference in cumulative protein release was measured. The polymer orientation of double-walled microspheres protected the microsphere morphology during PCL nerve guide fabrication. The microsphere core was composed of PLGA while the shell was PLLA, a polymer that is insoluble in ethyl acetate which was used to create the PCL/NaCl slurry. Nerve guides embedded with microspheres encapsulated with FITC-BSA show a homogeneous distribution of microspheres along the inner luminal circumference of the guide (FIG. 4A) and SEM analysis indicate that the mechanical integrity of the microspheres was maintained (FIG. 4B). Implantation of PCL nerve guides with GDNF in a rat sciatic nerve defect resulted in an increase in tissue integration in both the proximal and distal segments of the lumen of the nerve guide and an increase in Schwann cells in the distal region of the guide. Migration of Schwann cells toward double-walled microspheres indicates that bioactive GDNF was encapsulated and delivered to the internal environment of the nerve guide. The nerve guides created within this experiment indicate potential for examining the effect of a variety of growth factors within long gap peripheral nerve defects.

6.4 References

[1] Kim D, Midha R, Murovic J, Spinner R. Nerve injuries: operative results from major nerve injuries, entrapments, and tumors. 2nd ed. Philadelphia: Saunders Elsevier; 2008. pp. 1-611.

[2] Schlosshauer B, Dreesmann L, Schaller H-E, Sinis N. Synthetic nerve guide implants in humans: a comprehensive survey. Neurosurgery 2006; 59(4):740-8.

[3] Kemp S W P, Walsh S K, Midha R. Growth factor and stem cell enhanced conduits in peripheral nerve regeneration and repair. Neurol Res 2008; 30:1030-8.

[4] Midha R, Munro C, Dalton P, Tator C, Shoichet M. Growth factor enhancement of peripheral nerve regeneration through a novel synthetic hydrogel tube. J Neurosurg 2003; 99(3):555-65.

[5] Chavez-Delgado M E, Mora-Galindo J, Gomez-Pinedo U, Feria-Velasco A, Castro-Castaneda S, Lopez-Dellamary Toral F A, et al. Facial nerve regeneration through progesterone-loaded chitosan prosthesis. A preliminary report. J Biomed Mater Res B Appl Biomater 2003; 67B(2):702-11.

[6] Yang Y, De Laporte L, Rives C B, Jang J-H, Lin W-C, Shull K R, et al. Neurotrophin releasing single and multiple lumen nerve conduits. J Control Release 2005; 104(3):433-46.

[7] Fine E G, Decosterd I, Papaloizos M, Zurn A D, Aebischer P. GDNF and NGF released by synthetic guidance channels support sciatic nerve regeneration across a long gap. Eur J Neurosci 2002; 15(4):589-601.

[8] Bloch J, Fine E G, Bouche N, Zurn A D, Aebischer P. Nerve growth factor- and neurotrophin-3-releasing guidance channels promote regeneration of the transected rat dorsal root. Exp Neurol 2001; 172(2):425-32.

[9] Xu X, Yee W-C, Hwang P Y K, Yu H, Wan A C A, Gao S, et al. Peripheral nerve regeneration with sustained release of poly(phosphoester) microencapsulated nerve growth factor within nerve guide conduits. Biomaterials 2003; 24(13):2405-12.

[10] Rosner B I, Siegel R A, Grosberg A, Tranquillo R T. Rational design of contact guiding, neurotrophic matrices for peripheral nerve regeneration. Ann Biomed Eng 2003; 31(11):1383-401.

[11] Goraltchouk A, Scanga V, Morshead C M, Shoichet M S. Incorporation of protein-eluting microspheres into biodegradable nerve guidance channels for controlled release. J Control Release 2006; 110(2):400-7.

[12] Singh M, Morris C P, Ellis R J, Detamore M S, Berkland C. Microsphere-based seamless scaffolds containing macroscopic gradients of encapsulated factors for tissue engineering. Tissue Eng Part C Methods 2008; 14(4):299-309.

[13] Dodla M C, Bellamkonda R V. Differences between the effect of anisotropic and isotropic laminin and nerve growth factor presenting scaffolds on nerve regeneration across long peripheral nerve gaps. Biomaterials 2008; 29(1):33-46.

[14] Chen M-H, Chen P-R, Chen M-H, Hsieh S-T, Lin F-H. Gelatin-tricalcium phosphate membranes immobilized with NGF, BDNF, or IGF-1 for peripheral nerve repair: an in vitro and in vivo study. J Biomed Mater Res A 2006; 79A(4):846-57.

[15] Wood M, Borschel G, Sakiyama-Elbert S E. Controlled release of glial-derived neurotrophic factor from fibrin matrices containing an affinity-based delivery system. J Biomed Mater Res A 2009; 89A(4):909-18.

[16] Lee A C, Yu V M, Lowe J B, Brenner M J, Hunter D A, Mackinnon S E, et al. Controlled release of nerve growth factor enhances sciatic nerve regeneration. Exp Neurol 2003; 184(1):295-303.

[17] Newman J, Verity A, Hawatmeh S, Fee W J, Terris D. Ciliary neurotrophic factors enhances peripheral nerve regeneration. Arch Otolaryngol Head Neck Surg 1996; 122(4):399-403.

[18] Lewin S U, D S, Cheng E T, Verity A N, Terris D J. Simultaneous treatment with BDNF and CNTF after peripheral nerve transection and repair enhances rate of functional recovery compared with BDNF treatment alone. Laryngoscope 1997; 107(7):992-9.

[19] Willerth S M, Sakiyama-Elbert S E. Approaches to neural tissue engineering using scaffolds for drug delivery. Adv Drug Deliv Rev 2007; 59(4-5):325-38.

[20] Xu J-j, Chen E-y, Lu C-l, He C. Recombinant ciliary neurotrophic factor promotes nerve regeneration and induces gene expression in silicon tube—bridged transected sciatic nerves in adult rats. J Clin Neurosci 2009; 16(6):812-7.

[21] Kokai L E, Tan H, Jhunjhunwala S, Little S R, Frank J W, Marra K G. Protein bioactivity and polymer orientation is affected by stabilizer incorporation for double-walled microspheres. J Control Release, in press.

[22] Jiang C, Moore M, Zhang X, Klassen H, Langer R, Young M. Intravitreal injections of GDNF-loaded biodegradable microspheres are neuroprotective in a rat model of glaucoma. Mol Vis 2007; 13:1783-92.

[23] Kokai L E, Lin Y-C, Oyster N M, Marra K G. Diffusion of soluble factors through degradable polymer nerve guides: controlling manufacturing parameters. Acta Biomater 2009; 5(7):2540-50.

[24] Di Scipio F, Raimondo S, Tos P, Geuna S. A simple protocol for paraffin-embedded myelin sheath staining with osmium tetroxide for light microscope observation. Microsc Res Tech 2008; 71(7):497-502.

[25] Iwase T, Jung C G, Bae H, Zhang M, Soliven B. Glial cell line-derived neurotrophic factor-induced signaling in Schwann cells. J Neurochem 2005; 94(6):1488-99.

[26] Li L, Wu W, Lin L F, Lei M, Oppenheim R W, Houenou L. Rescue of adult mouse motoneurons from injury-induced cell death by glial cell line-derived neurotrophic factor. Proc Natl Acad Sci USA 1995; 92(21):9771-5.

[27] Iannotti C, Li H, Yan P, Lu X, Wirthlin L, Xu X-M. Glial cell line-derived neurotrophic factor-enriched bridging transplants promote propriospinal axonal regeneration and enhance myelination after spinal cord injury. Exp Neurol 2003; 183(2):379-93.

[28] Patel M, Mao L, Wu B, VandeVord P J. GDNF-chitosan blended nerve guides: a functional study. J Tissue Eng Regen Med 2007; 1(5):360-7.

[29] Li Q, Ping P, Jiang H, Liu K. Nerve conduit filled with GDNF gene-modified schwann cells enhances regeneration of the peripheral nerve. Microsurgery 2006; 26(2): 116-21.

[30] Deister C, Schmidt C. Optimizing neurotrophic factor combinations for neurite outgrowth. J Neural Eng 2006; 3(2):172-9.

[31] Paratcha G, Ledda F. GDNF and GFR[alpha]: a versatile molecular complex for developing neurons. Trends Neurosci 2008; 31(8):384-91.

[32] Gordon T. The role of neurotrophic factors in nerve regeneration. Neurosurg Focus 2009; 26(2):E3.
[33] Hoke A, Ho T, Crawford T O, LeBel C, Hilt D, Griffin J W. Glial cell line-derived neurotrophic factor alters axon schwann cell units and promotes myelination in unmyelinated nerve fibers. J Neurosci 2003; 23(2):561-7.
[34] Paratcha G, Ledda F, Ibanez C F. The neural cell adhesion molecule NCAM Is an alternative signaling receptor for GDNF family ligands. Cell 2003; 113(7): 867-79.

7 EXAMPLE: SUSTAINED GROWTH FACTOR DELIVERY PROMOTES AXONAL REGENERATION IN LONG GAP PERIPHERAL NERVE REPAIR

7.1 Materials and Methods

Reagents:

All chemicals were analytical grade or purer and were purchased from commercial suppliers. Poly(vinyl alcohol) (PVA; average Mw 9000-10,000, 80% hydrolyzed), poly(DL-lactide-coglycolide) (lactide:glycolide (50:50), Mw 40,000-75,000 units), PCL (Mw 65,000), dichloromethane, ethyl acetate, xylene, monoclonal anti-S100 and anti-Neurofilament, and phosphatebuffered saline (PBS) were all purchased from Sigma-Aldrich.Poly-L-lactide (0.90-1.20 dL/g) was purchased from Durect Corporation (Pelham, Ala.). The Masson's trichrome kit was purchased from American MasterTech. The GDNF Emax ImmunoAssay Systems Kit was purchased from Promega. Recombinant human GDNF produced in *Escherichia coli* was purchased from Leinco Technologies.

Fabrication of Nerve Guides with Double-Walled Microspheres:

Double-walled microspheres were prepared as previously described (11, 12). Briefly, a 17.5% poly(lactic-co-glycolic acid) (PLGA) solution was created with 150 mg PLGA in dichloromethane. In a separate glass scintillation vial, a 10% solution of poly(lactide) of equal polymer mass was prepared. A solution of 40 µL (0.1 mg/mL) of GDNF and human serum albumin in a 1:10 molar ratio was prepared in 0.5 mL sterile water over ice (formulation adapted from ref. 13). After mixing well, the solution was frozen and lyophilized. The protein/surfactant mixture was then added to PLGA already dissolved in dichloromethane and vortexed for *30 s to achieve a homogenous mixture. The PLGA solution was combined with the poly(lactic acid) (PLA) solution and vortexed for an additional 60 s. This oil-in-oil emulsion was added drop-wise through a Pasteur pipette to 200 mL of aqueous 0.5% PVA solution stirring at 900 rpm for 3 h. Then, the polymer microspheres were collected through centrifugation (1500 g for 10 min) and washed three times. Finally, the microspheres were lyophilized using a Labconco freeze dry system (without a cryoprotectant) and stored in a desiccant at −20° C. Twenty PCL nerve guides were fabricated using a modification of previously reported methods (14). Glass capillary mandrels were coated with a 17% w/v % aqueous solution of PVA, air-dried, and then immersed into the polymer slurry creating NaCl/PCL mandrel coatings. Microspheres (15 mg) were evenly spread onto a drawn grid on parchment paper (illustrated in ref. 11). After the first immersion of the glass mandrel into the PCL slurry, the ethyl acetate was allowed to evaporate for 30 s leaving a semi-hardened polymer layer on the mandrel. This was then smoothly rolled across the microspheres on parchment paper. The PCL with embedded microspheres was allowed to dry for 10 min and then repeatedly coated with additional layers of polymer as done in nerve guides without microspheres.

In Vitro Release of GDNF from Nerve Guides with Double-Walled Microspheres:

After fabrication, the guide was allowed to dry completely and NaCl leaching was performed by immersing the guides in sterile deionized (DI) water for 5 h. Nerve guides were removed from glass mandrels used during initial preparation and cut to 1.7-cm lengths. From this group of nerve guides, four were randomly selected for measuring in vitro GDNF release kinetics. The remaining 16 were implanted into the experimental group of animals. Long-term release studies were performed to approximate the amount of GDNF released during the duration of the in vivo studies. Nerve guides were individually added to clean eppendorf tubes. To each tube, 0.6 mL of PBS was added and the guides were incubated at 37° C. for specified time increments. To collect the releasate, the guides were removed from each eppendorf tube using clean forceps and added to clean tubes with fresh PBS. The amount of soluble GDNF from the collected samples was analyzed using an enzyme linked immunosorbent assay (ELISA) per manufacturer's instructions. The optical density was recorded at 450 nm in an ELISA plate reader (Tecan). The GDNF concentrations were calculated against a six-point standard curve, and then adjusted to picograms of GDNF per milligram of microspheres.

Surgical Methods:

Following the guidelines of the University of Pittsburgh Institutional of Animal Care and Use Committee, 48 male. Lewis rats (250-300 g, Harlan Labs) were used to evaluate the initial efficacy of GDNF released from PCL nerve guides for improved nerve regeneration. Each rat was anesthetized with an intraperitoneal injection of sodium pentobarbital (50 mg/kg). The sciatic nerve was exposed with a muscle splitting incision of the gluteal muscle. The nerve was sharply transected *0.5 cm from the proximal bifurcation and 0.5 cm of tissue was excised. After the proximal and distal nerve stumps were allowed to retract, the exposed fascicles were trimmed and sutured with 10-0 prolene epineurial mattress stitch 1 mm into each end of a 1.7-cm nerve guide, creating a 1.5-cm defect. The gluteal muscle and skin were then closed with 4-0 vicryl suture. The animals were randomly divided evenly amongst three groups, one of which received conduits with microspheres encapsulating GDNF and the other group received identical conduits with empty microspheres as a negative control. The third group of rats consisted of those which received a nerve isograft as a positive control; that is, nerve grafts from sacrificial rats of the same strain were used such that one donor animal produced two nerve grafts.

Functional Assessment of Nerve Regeneration:

Functional reinnervation of the lower limb muscles was assessed through three methods: video gait kinematics, gastrocnemius muscle twitch force, and gastrocnemius wet weight.

Video Gait Kinematics:

A high-speed (100 full frames per second) digital video camera (Basler A602f) was used to record motion of the hindlimb during walking along a 10-cm-wide runway (FIG. 10A). Black ink marks of contrast (3 mm diameter) or reflective markers (FIG. 10B) were positioned over the iliac crest, greater trochanter, knee, ankle, and fifth metatarsalphalangeal joints. During each test, the rat was positioned at one end and encouraged to walk the length of the 60-cm runway. This procedure is repeated until 15-20 steps were recorded with the rat walking straight forward (FIG. 10C). FIG. 11 shows an image taken from the high-speed video of a rat walking on the runway. A custom Matlab program was used to automatically track the location of each mark of contrast in all frames of the video. The marker locations were then used to construct line segments connecting each pair of adjacent markers. Intersegmental joint angles for the hip, knee, and ankle joints were calculated using Equation 1, which results from the dot product rule.

$$\theta = \frac{A \cdot B'}{|A||B|}$$

In this equation, the vectors A and B denote the line segments proximal and distal to the joint. The intersegmental angle (y) was computed as the inverse cosine of the dot product of vectors A and B, normalized by their respective lengths. The joint angle trajectories were computed from the measured marker positions. The foot touchdown and liftoff times were identified by visual inspection of the video and used to parse the swing (liftoff to touchdown) and stance (touchdown to liftoff) phases of the step cycle. The range of angular motion (maximum-minimum angles) for each joint was calculated during the swing and stance phases. These measures were then used for comparing gait kinematics across time points and treatment groups.

Gastrocnemius Twitch Force:

Immediately before sacrifice, animals were anesthetized with sodium pentobarbitol and the injured sciatic nerve was exposed with a muscle splitting incision made following the scar line remaining from graft or guide implantation. After freeing the isograft or regenerated nerve from the superficial and underlying muscle tissues, a bipolar nerve cuff electrode (1.5 mm diameter, Microprobe, Cat # NC (1.5)24) was placed around the nerve. Because the implanted nerve conduit enclosed the regenerated nerve, the PCL material had to be carefully removed such that sufficient nerve material was available for contact with the nerve cuff. The lower gastrocnemius was then completely isolated from the anterior and posterior tibialis muscles and the Achilles tendon was cut and fastened to a force transducer using a transfixation stitch and 4-0 silk sutures (FIG. 12). Finally, to completely stabilize the femur position, the animal's foot, knee, and back were immobilized on the data acquisition board using 16-0 gauge needles. Gastrocnemius twitch force was measured during stimulation of the sciatic nerve via the bipolar nerve cuff electrode. Tension in the suture connecting the gastrocnemius muscle to the force transducer was adjusted to obtain the maximum force. Stimulation pulses (200 ms wide; Model A320R; WPI) were applied at supramaximal intensity and the resulting twitch force was recorded at a sampling rate of 3 s (Model USB6009; National Instruments). The peak twitch force (relative to baseline) that was measured for five consecutive stimulation pulses was then calculated and optimized for the strongest stimulation points of contact between the nerve cuff and the sciatic nerve.

Gastrocnemius Muscle Weight:

After muscle force measurements, the animals were euthanized with an overdose of sodium pentobarbital (100 mg/kg intraperitoneal [IP]). A longitudinal incision in the lower leg parallel to the extension of the Achilles tendon and gastrocnemius (gastroc) muscle was made followed by a dissection of the skin which adequately exposed the gastroc muscle. The two proximal tendonous insertions of the gastroc in the femoral area were identification and sectioned. The distal gastroc insertion in the heel through the Achilles tendon was then severed for the extraction of the gastroc muscle. The muscle was then immediately weighed. The wet muscle mass of the unoperated contralateral control was compared to the muscle mass of the gastroc from the injured leg.

Histological Analysis:

After the animals were sacrificed the implanted guides or isografts were harvested and immediately immersed in a fixative. Nerves prepared for paraffin embedding for MTC stain and IHC were fixed in 4% paraformaldehyde. Samples prepared for histomorphometry analysis were fixed in 2.5% glutaraldehyde. After the tissue samples were treated with fixative for at least 24 h, the samples were washed with PBS and postfixed in 1% osmium tetroxide for either 2 h in sample preparation for MTC and IHC analysis or 24 h for those samples prepared for histomorphometry. Nerve specimens were then dehydrated with increasing concentrations of ethanol (30%-100%) and sectioned with a sharp razor blade at the proximal nerve stump, the proximal, middle, and distal regions of the nerve conduit, and at the distal nerve stump as described previously (11). The sections were then embedded in paraffin or epoxy in descending order and sectioned at thicknesses of 3 μm (IHC, MTC) or 0.5 μm (histomorphometry).

Masson's Trichrome:

For analysis of cellular and tissue infiltration of the nerve conduits, including collagen formation, nerve sections from the negative control and experimental animals were stained for Masson's Trichrome. Sectioned nerves were first deparaffinized with Xylene and rehydrated with decreasing percent alcohol solutions (100% followed by 90% and then DI water). Solutions from a Masson's trichrome kit were then used according to the protocol published by Di Scipio et al. (15).

Immunohistochemistry:

For fluorescent observation of Schwann cells, IHC was performed on explanted nerve samples. Paraffin-embedded specimens fixed in osmium tetroxide were first deparaffinized as described above and then etched with peroxide for 10 min as described in ref. 15 The samples were then blocked with 5% fetal bovine serum (FBS) with 0.02% triton-X in PBS for 1 h at room temperature. Antibodies against S-100 protein were then added overnight at 4° C. (1:400 in 2.5% FBS and 0.02% triton-X in PBS). The samples were then washed three times with PBS and the secondary antibody was added for 1 h at room temperature (1:1000 in 2.5% FBS and 0.02% triton-X in PBS). The samples were then washed thrice again and the nuclei were detected using 4',6-diamidino-2-phenylindole (0.6 μg/mL). The slides were then mounted with a fluorescent mounting media.

Histomorphometry:

Nerve guides were fixed using 2.5% glutaraldehyde, embedded in epon, and cut into 0.5-μm cross sections using an ultramicrotome (Reichert Ultracut). Sections were then mounted onto glass slides and stained with 1% toluidine blue dye for imaging. A Hitachi (model KP-M1AN) digitizing camera was mounted on a Zeiss Primo Star microscope for image acquisition. A 100× oil immersion objective lens was used to produce digital images at a final magnification of 1000×, with a pixel size of 0.125 μm as calibrated with a stage micrometer.

The Leco IA32 Image Analysis System (Leco) with custom calculation routines (macros) was used as developed by Hunter et al. 16 8-bit monochrome images were acquired and thresholded for determining myelin composition. As described by Hunter et al., manual adjustments were made to photomicrographs displayed on an attached monitor such that debris and nonviable nerve fibers were removed. Viable axons were defined as dark myelin rings enclosing clear fiber areas devoid of debris or cell nuclei. Myelin width, axon width, and fiber diameter were then automatically calculated through software analysis of red and green bit-plane identifiers. From these primary measurements, g-ratio (the ratio of the axonal diameter divided by the diameter of the axon and its myelin sheath) and nerve fiber density (fiber number/mm2) were calculated.

Statistical Analysis:

A minimum repetition value of four was used when measuring GDNF release from nerve guides. Results are expressed as the mean|standard deviation. Analysis of variance was used to determine statistical significance between experimental groups. The least significant difference method was used for multiple comparisons with $p<0.05$.

7.2 Results

GDNF Release from Nerve Guides with Double-Walled Microspheres:

Long-term release studies of GDNF from PCL nerve guides with double-walled microspheres were performed to approximate the release profile of the growth factor in vivo. Nerve guides embedded with double-walled microspheres encapsulating GDNF were incubated in PBS and released growth factor was quantified using an ELISA system. As shown in FIG. 3C, the release of GDNF from the PCL nerve guides did not exhibit the typical burst release profile seen in single-walled microsphere studies. At day 3, only *2.9% of the total released protein is liberated into solution. GDNF release is nearly linear until day 56, at which point *89.0% of the total growth factor is released. After this point, GDNF release is consistent to day 112, when the 16 week in vivo studies were complete. Assuming that the majority of microspheres weighed for nerve guide preparation were successfully embedded and secured into the nerve guide walls, the encapsulation efficiency for GDNF nerve guide production was ~1%.

Implantation of PCL Nerve Guides:

Upon exposure of the injured sciatic nerve at sacrifice, remaining PCL conduits were soft and pliable and both sutures intact. Nerve guides were well vascularized with a soft fibrous coating (FIG. 13A). The proximal and distal ends of the nerve guides were completely sealed with a fibrous capsule and small neuromas were apparent at both guide ends. Before separating the nerve guide from the regenerated nerve, a pinch test was administered proximal to any anastamosis to determine if a muscle reflex could be observed. In 75% of the animals treated with an empty PCL conduit (e.g., 12/16 rats), a lower limb reflex was observed. However, often the regenerated nerve through the negative control conduits was delicate, and attempts to remove the conduit for placement of a nerve cuff resulted in disruption in nerve continuity. It was also noted that the regenerating nerve grew adjacent or into the porous walls of the PCL conduit. Nerve guides implanted with GDNF releasing microspheres were also observed as well vascularized and sheathed in a soft fibrous coating. Results from a preliminary pinch test indicated that lower limb reinnervation was seen in 100% of the experimental animals. Furthermore, the nerves appeared to grow through the open lumen of the nerve guides and could be easily separated from the conduits for electrophysiology studies (FIG. 13B).

Functional Assessment of Nerve Regeneration: Video Gait Kinematics:

Gait kinematics from animals receiving a PCL nerve guide without growth factor (n¼ 3) and animals which received GDNF releasing guides (n¼ 16) after sciatic nerve injury are shown in FIG. 14. At the week 1 time point, all animals show a large reduction in the RoM at the ankle during the stance and swing phases; the stance-phase RoM for the knee was also reduced. Injured animals are unable to generate muscle force to extend the knee, reaching only ~90° of extension during stance (FIG. 14C) compared to 130° in the healthy animal. The ankle, which normally flexes ~70° to lift the foot during the swing phase, extends passively during swing after injury (FIG. 14E). To compensate for reduced motion at the ankle and knee, the hip joint shows a large increase in RoM as the hip is hyperflexed to provide sufficient ground clearance, compensating for the reduced motion at the ankle and knee. By week 15, the stance phase RoM for the ankle and knee return to baseline levels, and the RoM between experimental and negative control animals was not significantly different between groups at any time point.

Functional Assessment of Nerve Regeneration: Gastrocnemius Twitch Force:

The mean measured gastroc twitch force was 0.59±0.28 N, 0.44±0.22 N, and 0.07±0.07N for animals treated with an isograft (n=11), a nerve conduit with GDNF (n=6) and animals treated with a PCL conduit and no growth factors (n=7), respectively. The average twitch force between isograft animals and those within the experimental GDNF group was not significantly different (p=0.1754), whereas both of these groups showed significantly improved twitch force above negative control animals (FIG. 15).

Functional Assessment of Nerve Regeneration: Gastrocnemius Muscle Wet Weight:

The wet weight of recovered gastroc muscles from injured legs as normalized to contralateral uninjured controls are recorded in Table 1. The normalized values of muscles from animals treated with isografts as a positive control for nerve regeneration were statistically higher than both the experimental GDNF group as well as the PCL guides without growth factor delivery (p<0.01).

TABLE 1

RECORDED WET WEIGHTS OF INJURED
GASTROCNEMIUS MUSCLE AS NORMALIZED
TO CONTRALATERAL CONTROL

| Treatment description | Gastrocnemius wet weight (%) |
|---|---|
| Isograft (n = 11) | 46.6 ± 12.4[a] |
| PCL guide + GDNF (n = 7) | 24.8 ± 5.7 |
| Empty PCL guide (n = 6) | 21.7 ± 4.4 |

[a]Indicates statistical significance from experimental groups, p < 0.01.
PCL, poly(caprolactone);
GDNF, glial cell line-derived neurotrophic factor.

Figure 16A:
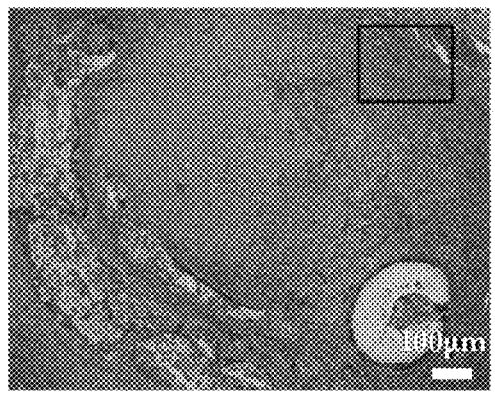
Figure 16B:
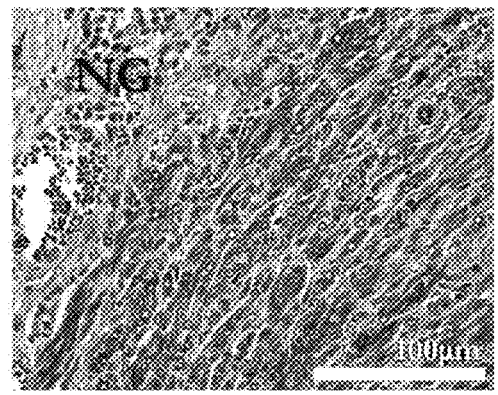
Figure 16C:
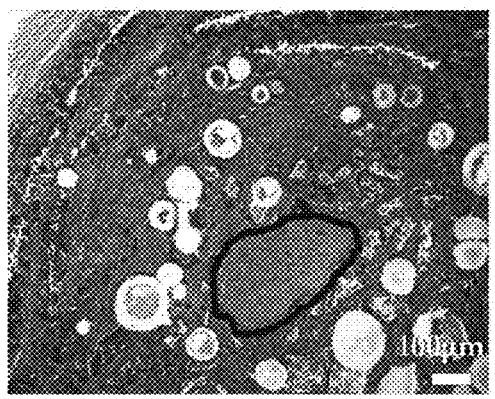
Figure 16D:
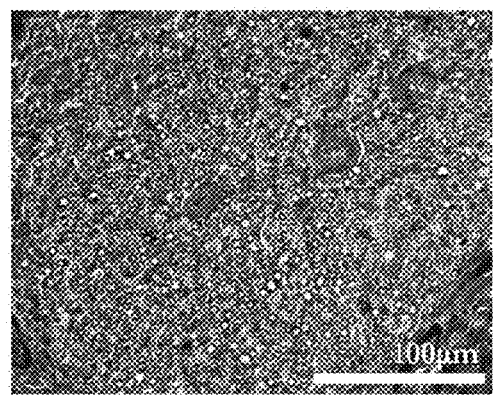

Histological Analysis: Masson's Trichrome:

The regeneration of nerve across a 1.5-cm defect was evaluated at 16 weeks. Low magnification transverse sections of the proximal portion of negative control conduits reveal a high degree of collagen content within the lumen of the guide (blue) with tissue integration throughout the entirety of the guide lumen (FIG. 16A). Regenerated nerve is evident near the PCL nerve guide wall (black box) and, as evident at higher magnification, is disorganized and sparse (FIG. 16B). Nerve tissue is also evident within the lumen of nerve guides releasing GDNF; however, fibers are located in the center of the lumen surrounded by newly formed tissue (black circle, FIG. 16C). High-magnification light micrographs reveal a large number of small nerve fibers that are well organized and thinly myelinated (FIG. 16D).

Low-magnification brightfield images of transverse sections from control PCL guides reveal that regenerated nerve tissue was not evident within mid (FIG. 17A) or distal segments (FIG. 17B). Tissue integration appears incomplete and few blood vessels are observed. However, in both the mid and distal regions of conduits releasing GDNF, there was regenerated nerve tissue within the lumen of the guides. Low magnification micrographs of the midline of explanted conduits (FIG. 17C) show collagen formation and tissue integration supporting the regenerated nerve fibers seen at higher magnification within FIG. 17D. Additionally, nerve tissue, including collagen and axons, is also evident within distal regions of the GDNF releasing conduits within both low (FIG. 17E) and high magnification (FIG. 17F) micrographs.

Figure 18A:
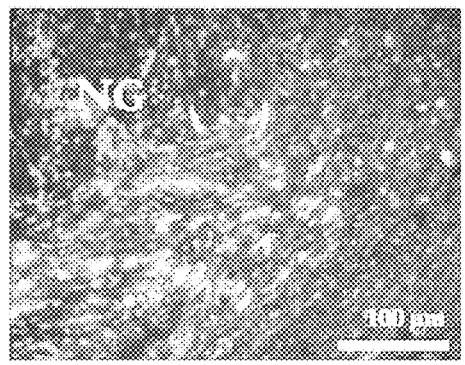
Figure 18B:
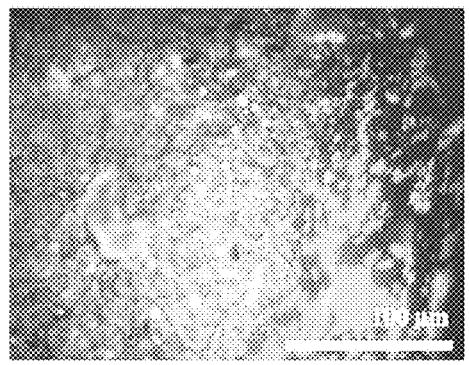
Figure 18C:
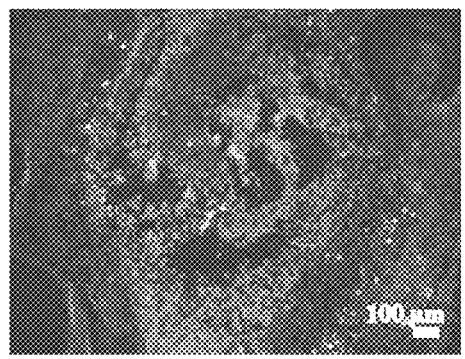
Figure 18D:
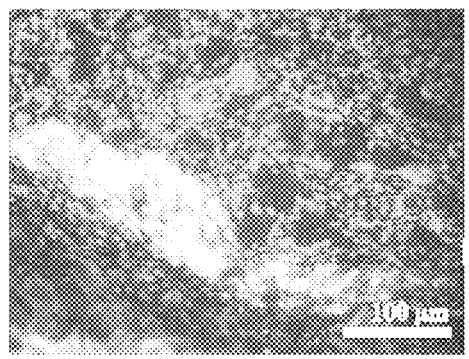
Figure 18E:
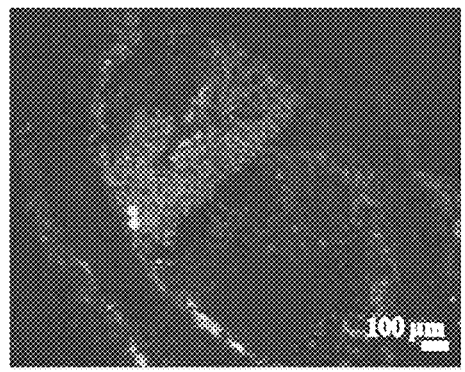
Figure 18F:
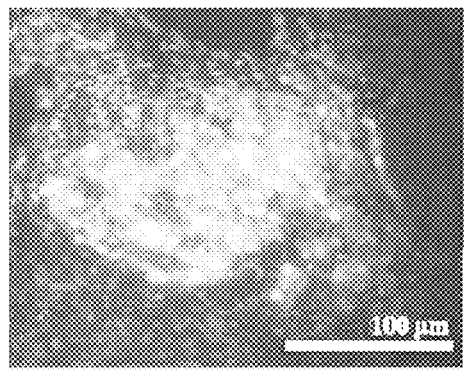

Histological Analysis: IHC:

Nerve tissue was evident in the proximal region of explanted conduits 16 weeks after sciatic nerve transection and conduit implantation. Fluorescent images reveal the presence of both nerve fibers (neurofilament proteins: green) and Schwann cells (S-100: red) in both negative control PCL guides and guides releasing GDNF. However, nerve tissue within control PCL guides (FIG. 18A) was localized to the internal border of the nerve guide wall and appears disorganized whereas nerve tissue was centrally located and well organized within GDNF releasing guides (FIG. 18B). Schwann cells and nerve fibers were not detectable within the middle (FIG. 18C) or distal segments (FIG. 18E) of control nerve guides, whereas robust Schwann cell populations were observed across the entire length of GDNF releasing guides (FIG. 18D, F).

Histological Analysis: G-Ratio and Nerve Fiber Density:

Monochrome images of the proximal nerve stump, proximal isograft or nerve guide, distal isograft or nerve guide, and distal nerve stump were acquired and thresholded to identify viable axons. Using semi-automated software, myelin width, axon width, and fiber diameter were calculated. From these primary measurements, g-ratio and nerve fiber density (fiber number/mm$^2$) were determined. Within the isograft-positive control nerve samples, the g-ratio of axons was consistent within each section from the proximal nerve stump to the distal nerve stump with a measured range of 0.40 to 0.42 (FIG. 19A). The g-ratio of nerve fibers within GDNF releasing guides were higher for all measured transverse sections, with average values of 0.55, 0.59, 0.56, and 0.53 for the proximal nerve stump, proximal graft or guide, middle graft or guide, and distal nerve stump sections, respectively, which are not statistically significantly different from within measured groups. These measured values from GDNF guides approach an uninjured g-ratio range of 0.6-0.7 (gray bar). Fibers from control PCL guides were observed to have a lower g-ratio value within both the proximal nerve stump (0.47) and the proximal segment (0.45) of the explanted nerve guide. No fibers were evident in the mid or distal regions of negative control PCL guides for measurement calculations.

Evaluation of nerve fiber density throughout the length of explanted nerve samples reveals an increased density of fibers per mm$^2$ for both the GDNF and control nerve guides as compared to isograft positive controls, an indication of nerve regeneration (FIG. 19B). As seen in fiber g-ratio results, isograft sections had a small range of fiber densities (~11,300-12,200) progressing from the proximal to the distal nerve stumps, indicating limited axonal sprouting occurred within the graft The density of fibers within GDNF releasing guides was higher than negative control guides for all measured segments and there were no viable nerve fibers in negative control nerve guides beyond the mid region of the explanted conduits.

7.3 Discussion

The efficacy of GDNF toward improving peripheral nerve regeneration through nerve guidance conduits has been evaluated in vivo. Patel et al. reported chitosan scaffolds blended with laminin-1 and 5 µg GDNF were implanted across a 10-mm gap in the Lewis rat sciatic nerve (9). After 12 weeks, the chitosan/GDNF guides resulted in decreased gastrocnemius muscle atrophy and restoration of functional strength that was comparable to autograft controls. Behavioral testing indicated that GDNF treatment groups regained sensation and improved gait kinematics. In addition, silicone conduits filled with GDNF gene-modified Schwann cells have resulted in significantly improved nerve conduction velocity, number and density of regenerated nerves, and the thickness of the myelin sheath of regenerated nerves than that seen in controls across a 10-mm defect in the Wistar rat (10). Finally, nerve guides with a GDNF releasing rod increased the number of myelinated axons and the overall number of regenerated axons was four-fold higher than nerve guides with nerve growth factor (7). Experiments examining GDNF release from nerve guides for 6 weeks suggested that bioactive GDNF was delivered to endogenous cell populations and markedly improved cellular integration and tissue formation across the nerve injury (11). Although nerve gaps treated with empty microsphere conduits resulted in incomplete fibrotic tissue formation in the center of proximal segment of excised nerve guides, nerve guides releasing GDNF had an increase in cellular infiltration and tissue integration within the lumen of the conduits. Additionally, we observed an increase in cellular infiltration and collagen content after GDNF treatment, and we hypothesize that this lead to an improved scaffold for Schwann cell migration and supported axonal outgrowth within this longer 16-week in vivo study. Within this study, we have shown that GDNF is released from nerve guides in vitro for over 100 days. When implanted into rat sciatic nerve defects, a higher density of nerve tissue regenerated through the center of conduits as opposed to negative control guides (e.g., empty microsphere PCL conduits), which produced nerve tissue bolstered by the wall of the nerve guide. Regenerated nerve tissue from within GDNF releasing guides appeared to have an increased level of collagen and intercellular tissue as observed with MTC. Quantification of high magnification light micrographs through software analysis supported visual impressions of improved nerve repair with GDNF treatment. Animals receiving GDNF had a g-ratio that approached native, uninjured levels, and were improved above both isografts and negative controls. Additionally, the mean nerve fiber density of regenerated nerves was highest within conduits releasing GDNF, and was statistically higher than isograft controls at the proximal end of conduits ($p<0.05$). Finally, immunofluorescent micrographs identifying Schwann cells show a large population of Schwann cells throughout the length of conduits releasing GDNF, whereas very few Schwann cells are detectable in the middle and distal segments of negative control guides. The presence of Schwann cells within the lumen of the guides is a positive indication for nerve repair, as several studies have shown that higher numbers of Schwann cells result in more robust nerve regeneration (17-19). Analysis of muscle reinnervation through quantification techniques of rat gait proved challenging using the techniques described herein. While mass loss was statistically equivalent when comparing wet muscle weight in GDNF treated and empty nerve guides, muscle function through twitch force may be more indicative of nerve regrowth and reinnervation of target end organs. This study suggests that measuring muscle twitch force is an improved method of observing nerve regeneration to target muscles over the described timepoint of 15 weeks. It is very possible that at a longer timepoint, the muscle wet weights between the control and experimental groups would have been different due to the continued lack of nerve innervation in the gastrocnemius muscle of rats treated with empty nerve guides. No significant difference in joint angle RoM was measured between the GDNF experimental group and the negative control. The development of a technique for analyzing gait kinematics through video recording was undertaken as a method of circumventing those challenges seen with sciatic functional index measurement (20). However, unique obstacles were presented within this method of gait analysis. First, animal behavior is varied, and often animals were observed as walking with a unique head position, speed, or step pattern. In addition, animals would traverse the walkway only a few times before losing interest in the activity and could not be trained to proceed with a smooth gait pattern despite incentives provided by the operator. Because of this, step cycles were used for measuring joint angles from only those steps that were consecutive and were determined to be of a walking nature (at least one foot always on the ground). The use of a treadmill would greatly improve the consistency seen in joint angle measurements and may allow this technique to be a more robust method for detecting early improvements in gait kinematics after lower limb nerve injury.

Within this study, we have shown that GDNF can be successfully encapsulated in double-walled microspheres and released in a controlled manner from PCL nerve guides for over 100 days in vitro and improves nerve regeneration in vivo. Upon the initial exposure of the site of nerve injury, nerve tissue was observed exiting the distal end of implanted conduits in only 70% of the control PCL guides, whereas 100% of the animals implanted with GDNF releasing guides had nerve trunks throughout the length of the conduits and integrating into the distal target muscles. In addition, the measured gastrocnemius twitch force, an indication of muscle atrophy and reinnervation, was significantly improved by a difference of sixfold in animals treated with GDNF releasing conduits as opposed to those that received empty PCL conduits. Markedly, the twitch force between animals treated with isografts, considered to be the gold standard for nerve repair, was not significantly different from animals receiving GDNF releasing conduits. Although this study evaluated nerve repair after treatment with a single growth factor, the nerve guide design is modular; therefore, these PCL conduits described herein lend themselves easily toward investigation of a variety of different therapeutics for improved nerve regeneration.

7.4 References

1. Schlosshauer, B., Dreesmann, L., Schaller, H.-E., and Sinis, N. Synthetic nerve guide implants in humans: a comprehensive survey [review]. Neurosurgery 59, 740, 2006.
2. Valero-Cabré , A., Tsironis, K., Skouras, E., Perego, G., Navarro, X., and Neiss, W. Superior muscle reinnervation after autologous nerve graft or poly-L-lactide-epsilon-caprolactone (PLC) tube implantation in comparison to silicone tube repair. J Neurosci Res 63, 214, 2001.
3. Pfister, L. A., Papaloizos, M., Merkle, H. P., and Gander, B. Nerve conduits and growth factor delivery in peripheral nerve repair. J Peripher Nery Syst 12, 65, 2007.
4. Iwase, T., Jung, C., Bae, H., Zhang, M., and Solivan, B. Glial Cell Line Derived Neurotrophic Factor-Induced Signaling in Schwann Cells. J Neurochem 94, 1488, 2005.
5. Li, L., Wu, W., Lin, L., Lei, M., Oppenheim, R., and Houenou, L. Rescue of Adult Mouse Motomeurons from Injury-Induced Cell Death by Glial Cell Line-Derived Neurotrophic Factor. Proc Natl Acad Sci 92, 9771, 1995.
6. Iannotti, C., Li, H., Yan, P., Lu, X., Wirthlin, L., and Xu, X. Glial cell line-derived neurotrophic factor-enriched bridging transplants promote propriospinal axonal regeneration and enhance myelination after spinal cord injury. Exp Neurol 183, 379, 2003.
7. Fine, E. G., Decosterd, I., Papaloizos, M., Zum, A. D., and Aebischer, P. GDNF and NGF released by synthetic guidance channels support sciatic nerve regeneration across a long gap. Eur J Neurosci 15, 589, 2002.
8. Barras, F., Pasche, P., Bouche, N., Aebischer, P., and Zum, A. D. Glial cell line-derived neurotrophic factor released by synthetic guidance channels promotes facial nerve regeneration in the rat. J Neurosci Res 70, 746, 2002.
9. Patel, M., Mao, L., Wu, B., and VandeVord, P. J. GDNFchitosan blended nerve guides: a functional study. J Tissue Eng Regen Med 1, 360, 2007.
10. Li, Q., Ping, P., Jiang, H., and Liu, K. Nerve conduit filled with GDNF gene-modified schwann cells enhances regeneration of the peripheral nerve. Microsurgery 26, 116, 2006.
11. Kokai, L. E., Ghaznavi, A. M., and Marra, K. G. Incorporation of double-walled microspheres into polymer nerve guides for the sustained delivery of glial cell line-derived neurotrophic factor. Biomaterials 31, 2313, 2010.
12. Kokai, L. E., Tan, H., Jhunjhunwala, S., Little, S. R., Frank, J. W., and Marra, K. G. Protein bioactivity and polymer orientation is affected by stabilizer incorporation for double-walled microspheres. J Controlled Release 25, 168, 2010.
13. Jiang, C., Moore, M., Zhang, X., Klassen, H., Langer, R., and Young, M. Intravitreal injections of GDNF-loaded biodegradable microspheres are neuroprotective in a rat model of glaucoma. Mol Vis 13, 1783, 2007.
14. Kokai, L. E., Lin, Y.-C., Oyster, N. M., and Marra, K. G. Diffusion of soluble factors through degradable polymer nerve guides: Controlling manufacturing parameters. Acta Biomaterialia 5, 2540, 2009.
15. Di Scipio, F., Raimondo, S., Tos, P., and Geuna, S. A simple protocol for paraffin-embedded myelin sheath staining with osmium tetroxide for light microscope observation. Microsc. Res Tech 71, 497, 2008.
16. Hunter, D. A., Moradzadeh, A., Whitlock, E. L., Brenner, M. J., Myckatyn, T. M., Wei, C. H., Tung, T. H. H., and Mackinnon, S. E. Binary imaging analysis for comprehensive quantitative histomorphometry of peripheral nerve. J Neurosci Methods 166, 116, 2007.
17. Rutkowski, G. E., Miller, C. A., Jeftinija, S., and Mallapragada, S. K. Synergistic effects of micropatterned biodegradable conduits and Schwann cells on sciatic nerve regeneration. J Neural Eng 1, 151, 2004.
18. Kim, S.-M., Lee, S.-K., and Lee, J.-H. Peripheral nerve regeneration using a three dimensionally cultured Schwann cell conduit. J Craniofac Surg 18, 475, 2007.

19. Guenard, V., Kleitman, N., Morrissey, T. K., Bunge, R. P., and Aebischer, P. Syngeneic Schwann cells derived from adult nerves seeded in semipermeable guidance channels enhance peripheral nerve regeneration. J Neurosci 12, 3310, 1992.
20. Brown, C. J., Mackinnon, S. E., Evans, P. J., Bain, J. R., Makino, A. P., Hunter, D. A., and Hare, G M T. Self-evaluation of walking-track measurement using a sciatic function index. Microsurgery 10, 226, 1989.

The publication Biomaterials 31 (2010) p. 2313-2322, available online on Dec. 7, 2010 is incorporated by reference in its entirety. The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A method of promoting nerve generation comprising implanting an implantable nerve guide comprising a biodegradable polymer tube having a lumen comprising:

(a) an inner layer comprising a biodegradable polymer, into which are embedded double-walled microspheres containing glial cell-line derived neurotrophic factor, wherein a poly(lactic-co-glycolic acid) layer forms a core and a poly(lactide) layer forms a shell of the double-walled microsphere and the double-walled microspheres provide sustained release of the glial cell-line derived neurotrophic factor over at least seven days in an amount effective in promoting nerve regeneration; and (b) an outer layer comprising a biodegradable polymer without double-walled microspheres, wherein said outer layer encapsulates the inner layer.

2. The method of promoting nerve generation of claim 1, wherein the inner layer comprising a biodegradable polymer layer comprises poly(caprolactone).

3. The method of promoting nerve generation of claim 1, wherein the inner layer comprising a biodegradable polymer layer comprises poly(caprolactone) and the outer layer comprising a biodegradable polymer comprises poly(caprolactone).

* * * * *